United States Patent [19]

Alkon et al.

[11] Patent Number: 5,580,748

[45] Date of Patent: Dec. 3, 1996

[54] DIAGNOSTIC TESTS FOR ALZHEIMERS DISEASE

[75] Inventors: Daniel L. Alkon, Bethesda; Rene Etcheberrigaray, Rockville; Etsuro Ito, Chevy Chase, all of Md.; Gary E. Gibson, Larchmont, N.Y.

[73] Assignee: The United States of America as represented by the Department of Health and Human Services, Washington, D.C.

[21] Appl. No.: 56,456

[22] Filed: May 3, 1993

[51] Int. Cl.$^6$ .............................. C12Q 1/02; C12Q 1/00
[52] U.S. Cl. .................. 435/29; 435/4; 436/811
[58] Field of Search .................. 435/29, 4, 968; 436/63, 811

[56] References Cited

U.S. PATENT DOCUMENTS 4,925,664  5/1990  Jackson .................................. 424/537

FOREIGN PATENT DOCUMENTS 8909600  10/1989  WIPO .

OTHER PUBLICATIONS

Etcheberrigaray R., Potassium Channel Dysfunction . . . Proc Natl Acad Sci, vol. 90 pp. 8209–8213 1993.
Adunsky A., Increased Cytosolic Free Calcium In Lymphocstes . . . J Of Nguroimm 33 (1991) 167–172.
Ikeda, M., Selective Reduction of $^{125}$I Apamin Binding . . . Brain Research 567 (1991) 51–56.
Crespo D., The Influence Of Age On Supraoptic . . . Mech Of Ageing & Development 62 (1992) 223–228.
Etcheberrigaray R., Potassium Channel Dysfunction . . . Proc Natl Acad Sci USA 90 (1993) 8209–8213.
E. Ito et al., (1993) Neuroscience Research, vol. 18: Abstract 615 "A laboratory diagnosis of Alzheimer's Disease with Patch–Clamp and $Ca^{2+}$–imaging techniques".
R. Etcheberrigaray et al. (1993) Proceedings Of The National Academy Of Sciences (USA) vol. 90, No. 17. 8209–8213 "Potassium channel dysfunction in fibroblasts identifies patients with Alzheimer disease."
E. Ito et al. (1994) Proceedings Of The National Academy Of Sciences (USA) vol. 91, No. 2, pp. 534–538 "Internal Ca2+ mobilization is altered in fibroblasts from patients with Alzheimer disease".

H–M. Huang et al. (1994) Neurobiology Of Aging, vol. 12: pp. 469–473 "Inositol Phosphates and Intracellular Calcium After Bradykinin Stimulation in Fibroblasts From Young, Normal Aged and Alzheimer Donors".
A. Grossmann et al., (1993) Neurobiology Of Aging, vol. 14, No. 2: 177–185 "Intracellular Calcium Response Is Reduced in CD4+ Lymphocytes in Alzheimer's Disease and in Older Persons with Down's Syndrome".
B. Sakmann et al. (1984) Ann. Rev. Physiol., vol. 46: 455–472 "Patch Clamp Techiques for Studying Ionic Channels in Excitable Membranes".
C. Peterson et al. (1988) Neurobiology Of Aging, vol. 9, No. 3: 261–266 "Altered response of Fibroblasts From Aged and Alzheimer Donors to Drugs That Elevate Cytosolic Free Calcium".
A. F. Ghuysen–Itard et al. (1993) Gerontology, vol. 39: 163–169 "Loss of Calcium–Homeostatic Mechanisms in Polymorphouclear Leukocytes of Demented and Nondemented Elderly Subjects".
Etcheberrigaray, R. et al., *Soc. Neurosci Abstract*, vol. 18, Oct. 25–30, 1992 "Distinguishing Features of Potassium Channels in Fibroblasts From Alzheimer Aged and Young Donors".
Dewar, D. et al., *Neurobiol. Aging.* vol. 13 (Suppl. 1), Jul. 12–17, 1992 "Multiple Ion Channel Binding Sites are Differentilly Altered in Alzheimer's Disease Cortex".
Ikeda, M. et al. *Brain Res.* vol. 567, pp. 51–56 (1991) "Selective Reduction of Iodine–125 Apamin Binding Sites in Alzheimer's Hippocampus: A Quantitative Autoradiographic Study".
Etcheberrigaray, R. et al. *Proc. Nat'l Ac. Sciences*, vol. 89, pp. 7184–7188 (1992) "Classical Conditioning and Protein Kinase C Activation Regulate the Same Single Potassium Channel in Hermissenda Crassicornis Photoreceptors".
Sakmann, B. and Neker, E., *Ann. Rev. Physiol.* vol. 46, pp. 455–472 (1984) "Patch Clamp Techniques For Studying Ionic Channels in Excitable Membranes".

*Primary Examiner*—Ralph J. Gitomer
*Attorney, Agent, or Firm*—Morgan & Finnegan LLP

[57] ABSTRACT

The present invention is a method for the diagnosis of Alzheimer's disease using human cells. Specifically, the method detects differences between potassium channels in cells from Alzheimer's patient and normal donors, and differences in intracellular calcium concentrations between Alzheimer's and normal cells in response to chemicals known to increase intracellular calcium levels.

24 Claims, 14 Drawing Sheets

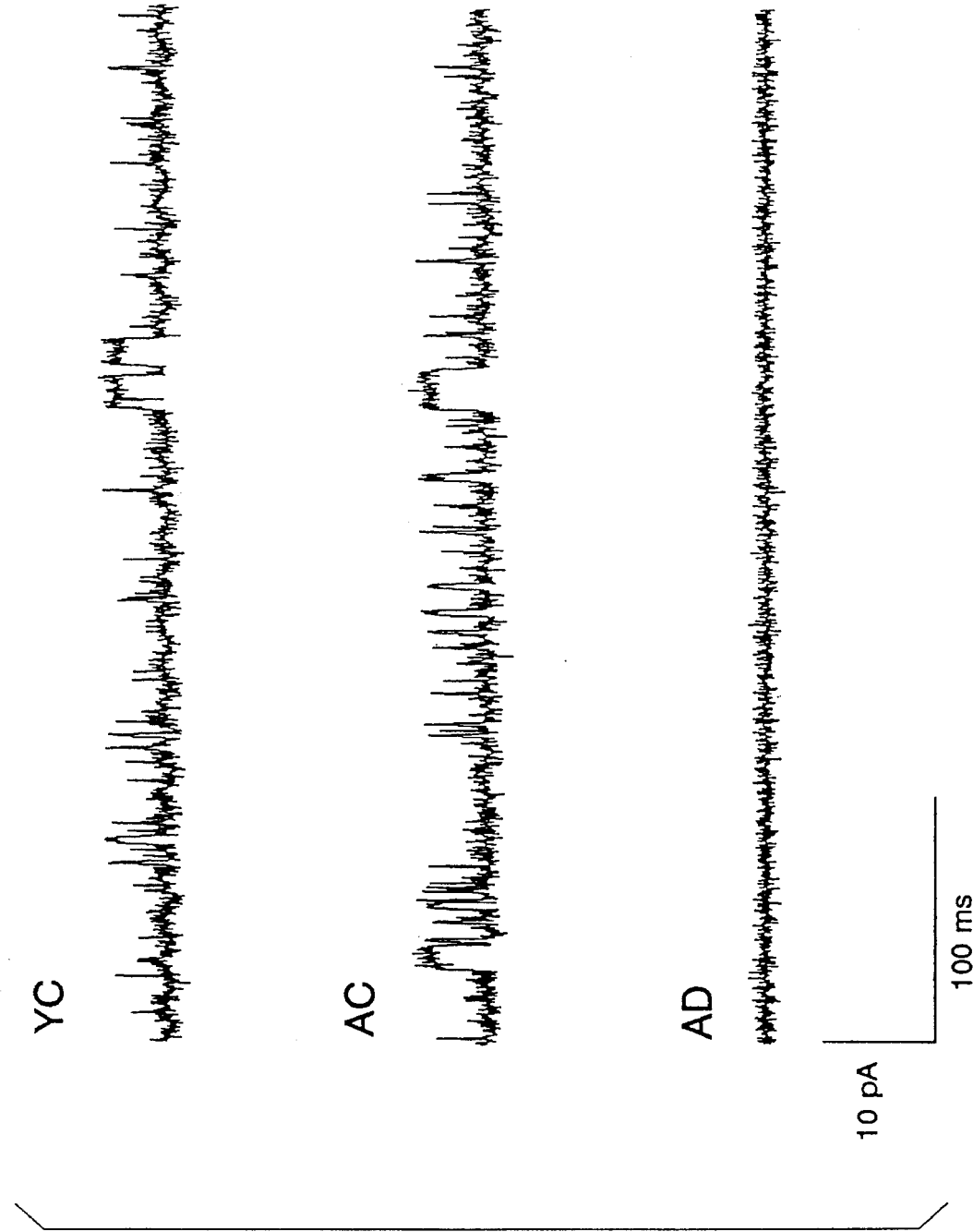

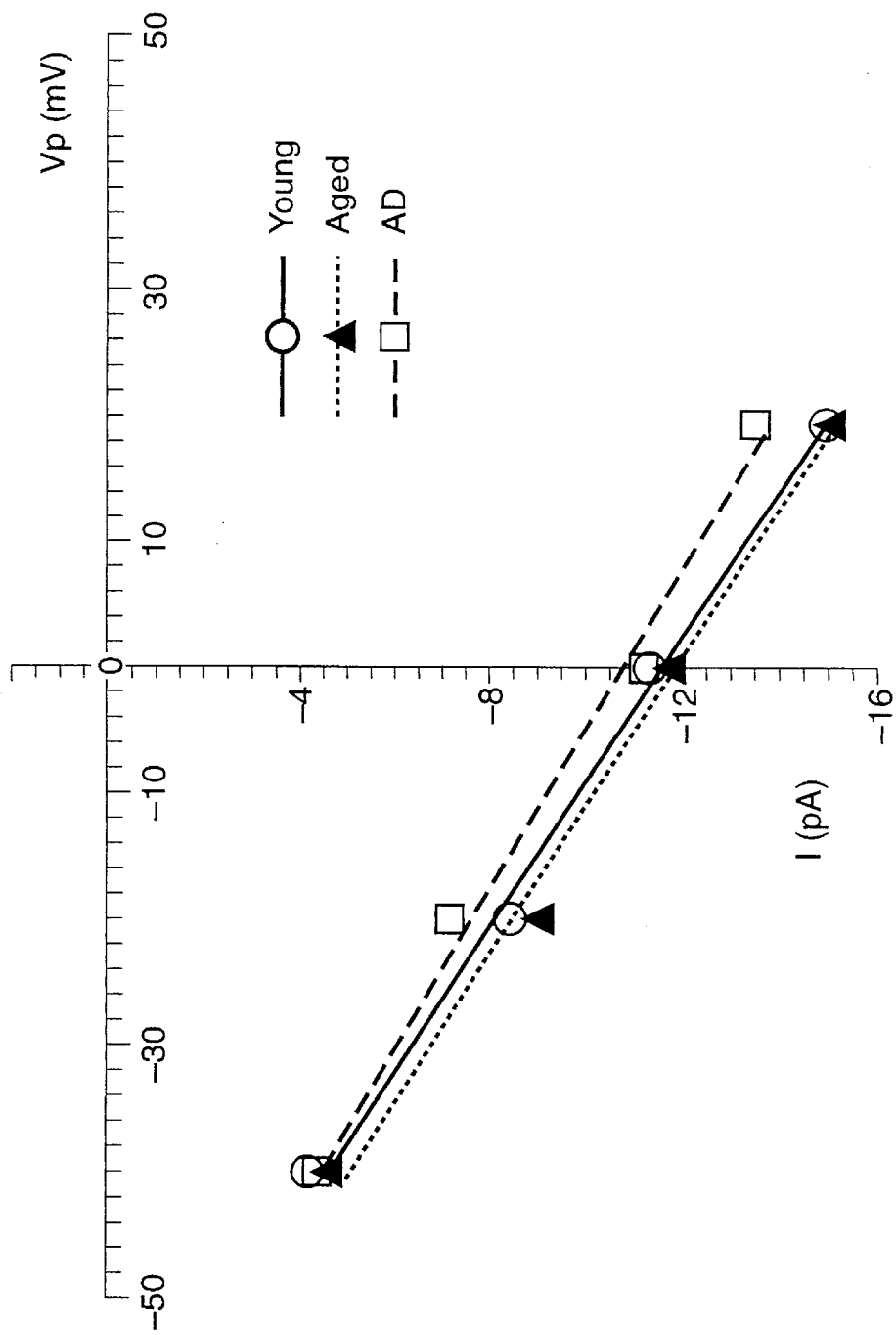

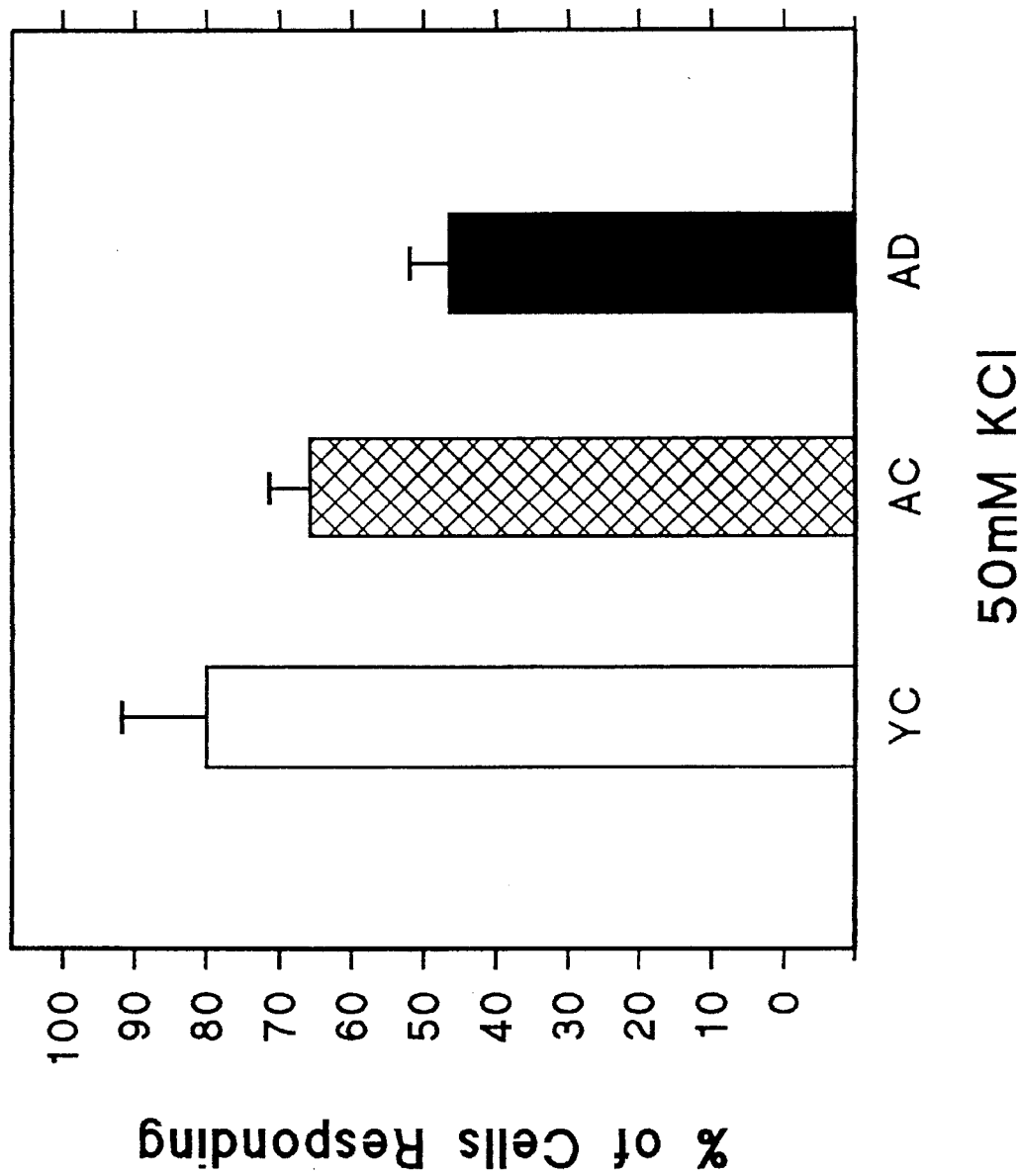

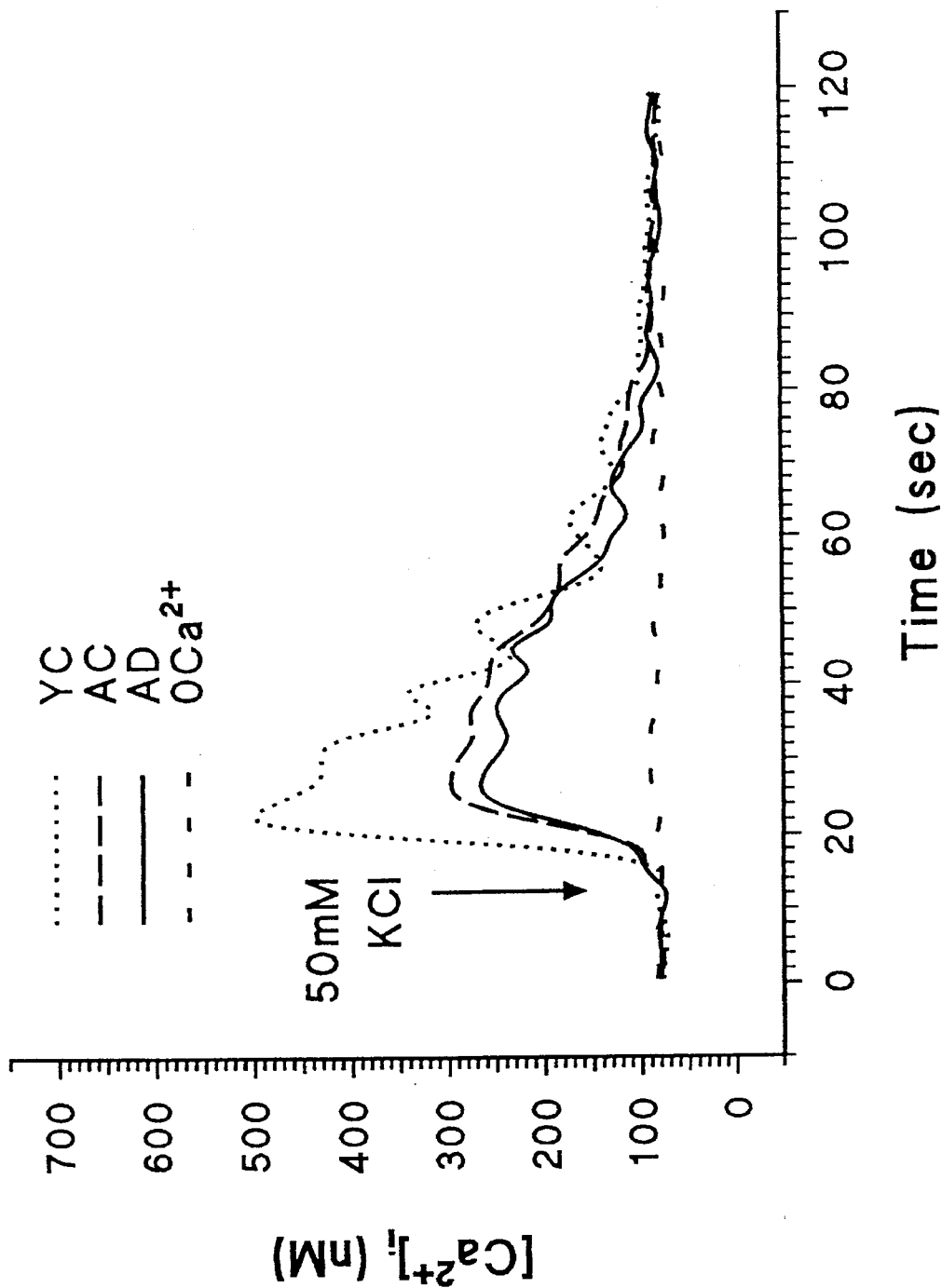

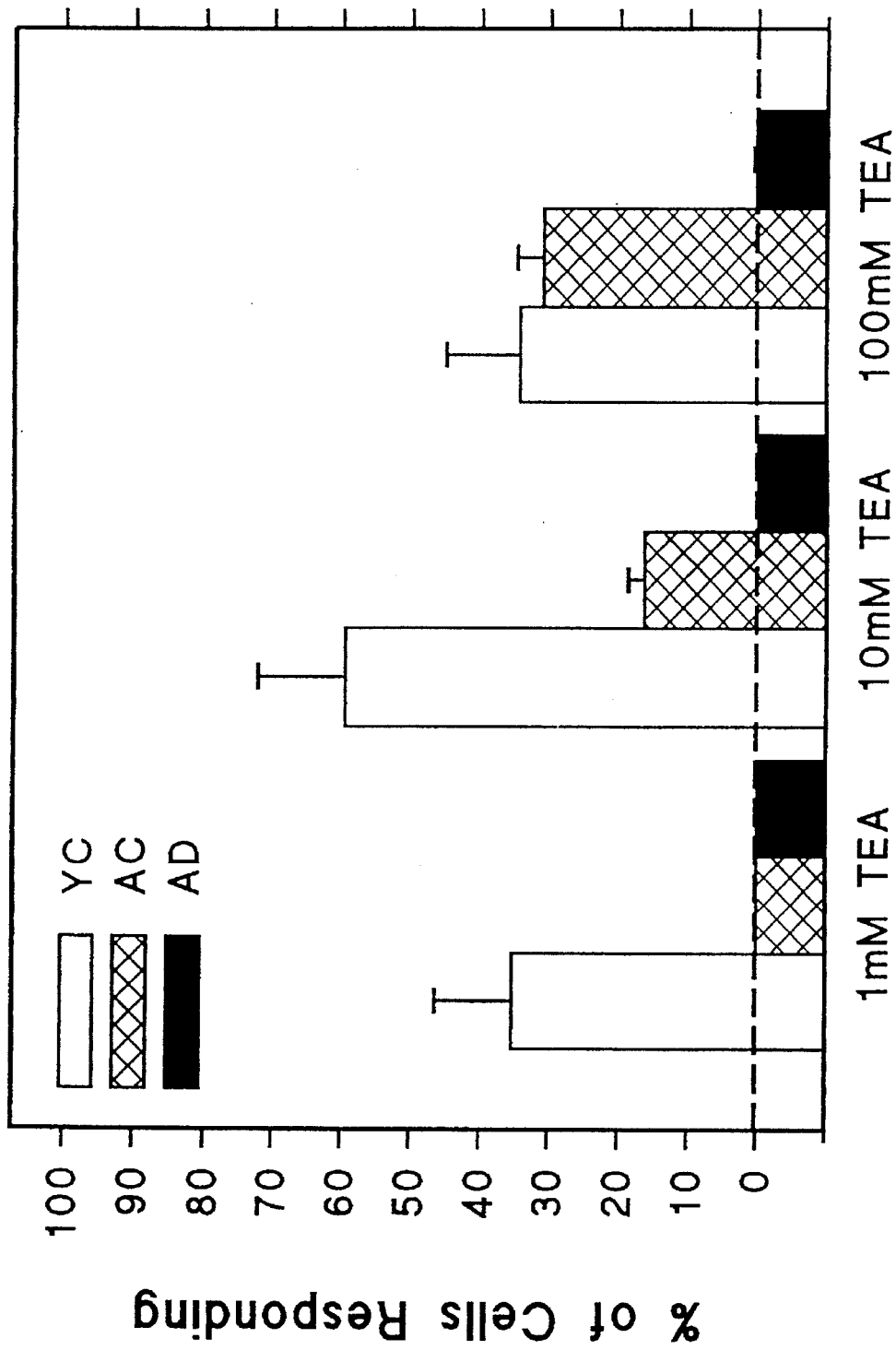

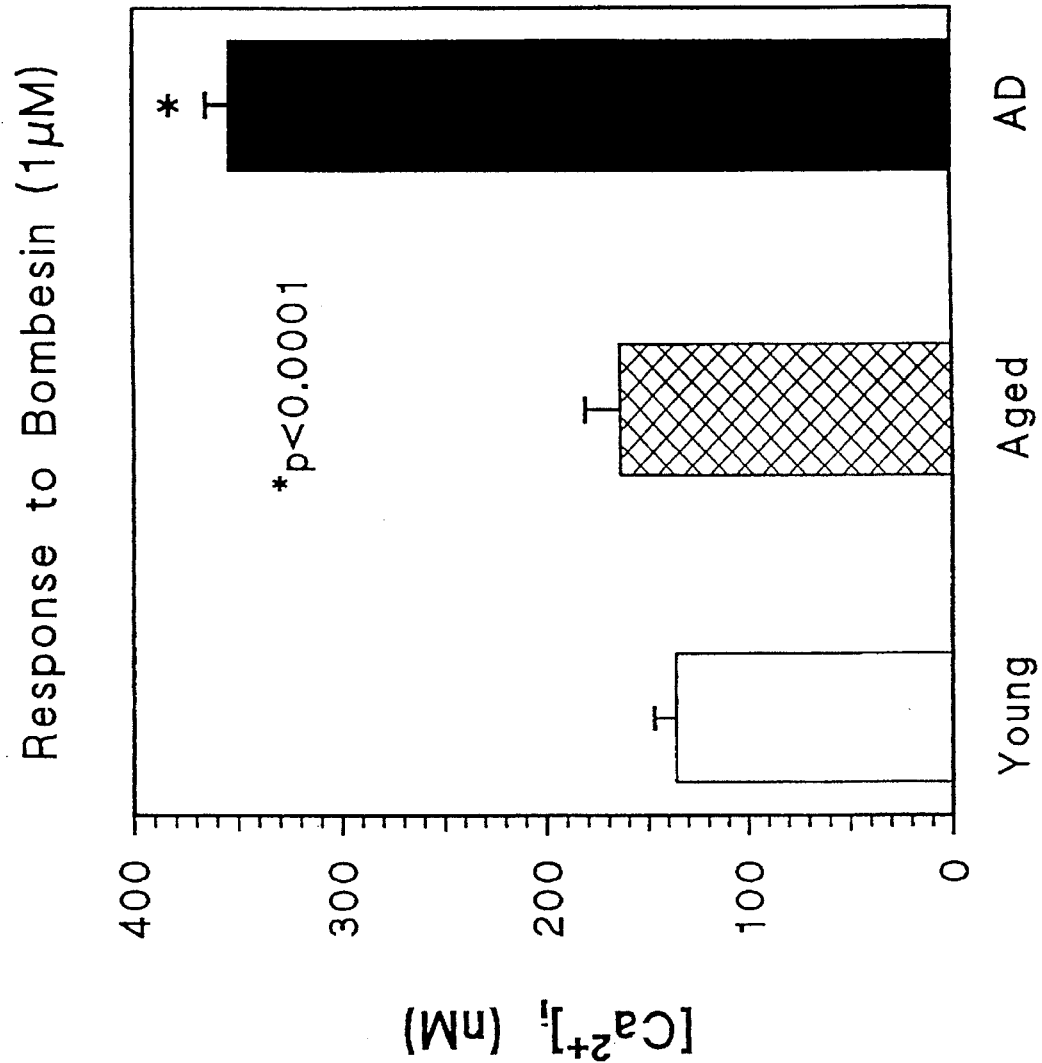

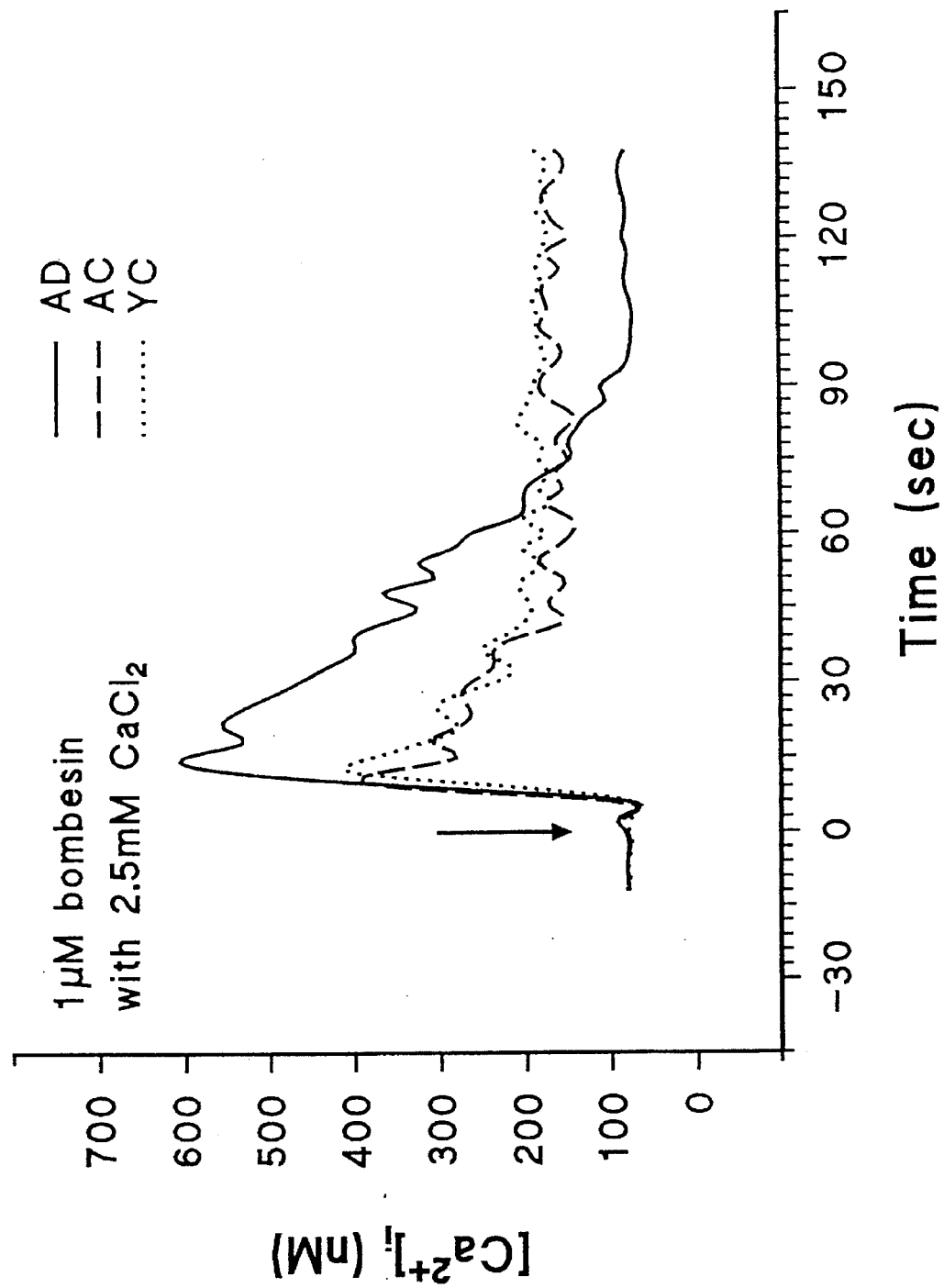

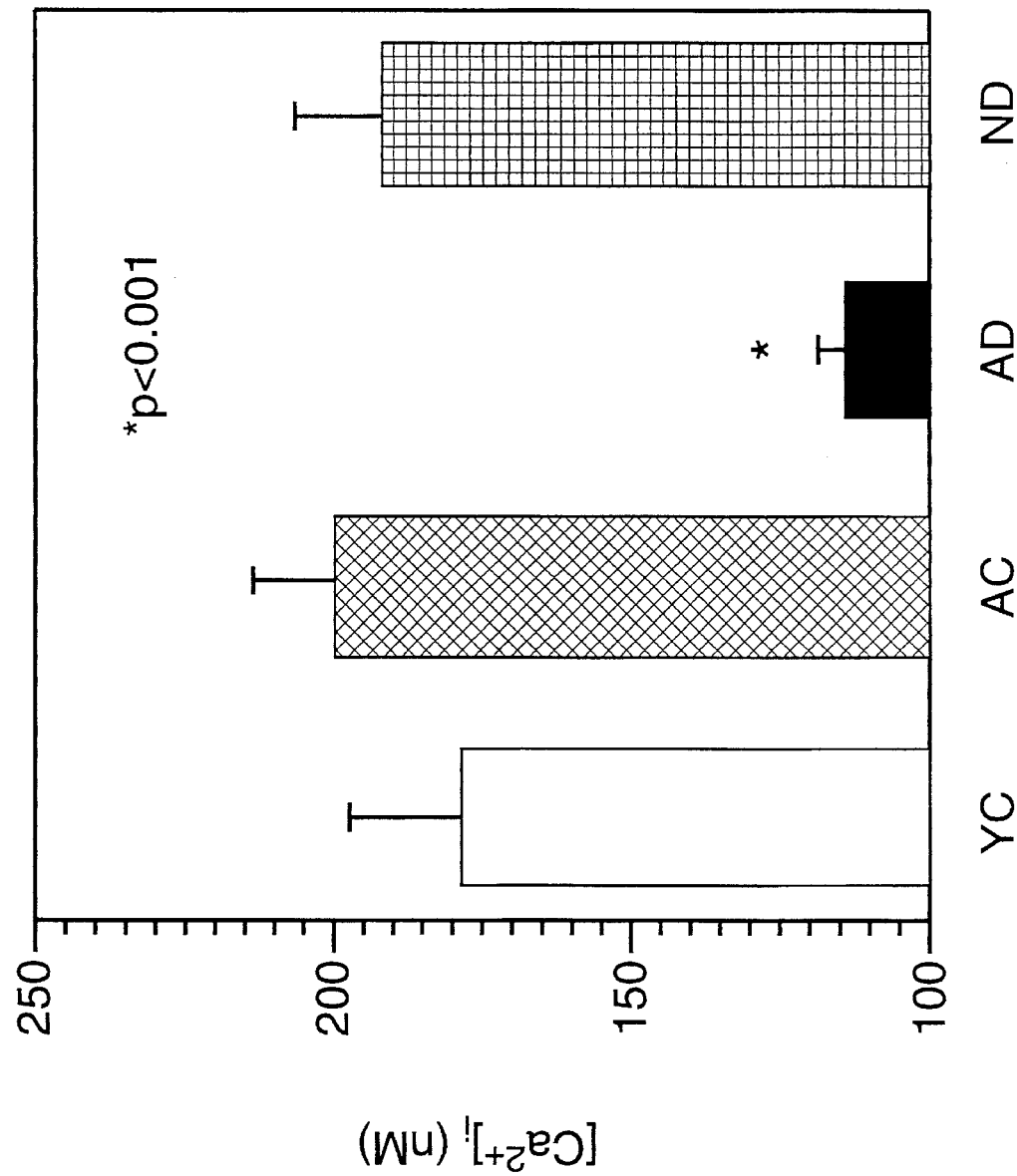

DIAGNOSTIC TESTS FOR ALZHEIMERS DISEASE

FIELD OF THE INVENTION

The present invention relates to methods for diagnosing Alzheimer's disease. The technique utilizes newly discovered differences between cells from healthy donors and those with Alzheimer's disease. In one method, differences in the existence of functional potassium channels are assessed. In another method, differences in intracellular calcium levels in response to depolarization by a potassium channel blocker are assessed. In yet another method, differences in intracellular calcium levels in response to a chemical known to increase intracellular calcium levels by releasing calcium from intracellular stores are assessed.

BACKGROUND OF THE INVENTION

Alzheimer's disease is associated with extensive loss of specific neuronal subpopulations in the brain (Sims, N. R., et al. (1987) *Annals of Neurology* 21:451), with memory loss being the most universal symptom. (Katzman, R. (1986) *New England Journal of Medicine* 314:964). Alzheimer's disease has been linked to a genetic origin. (Schellenberg, G. D., et al. (1992) *Science* 258:668; Li, G., et al. (1991) *Psychiatric Clinics of North America* 14:267; St. George-Hyslop, P. H., et al. (1989) *Neurobiology of Aging* 10:417; St. George-Hyslop, P. H., et al. (1987) *Science* 235:885). Early-onset familial forms of the disease exhibit a genetic defect on chromosome 21. (St. George-Hyslop, P. H., et al. (1987)).

Cellular changes, leading to neuronal loss and the underlying etiology of the disease, remain unknown. Proposed causes include environmental factors, (Perl, D. P. (1985) *Environmental Health Perspective* 63:149; Katzman, R. (1986)), including metal toxicity, (Perl, D. P., et al. (1980) *Science* 208:297), defects in β-amyloid protein metabolism, (Shoji, M., et al. (1992) *Science* 258:126; Joachim, C. L. and Selkoe, D. J. (1992) *Alzheimer Disease Assoc. Disord.* 6:7; Kosik, K. S. (1992) *Science* 256:780; Selkoe, D. J. (1991) *Neuron* 6:487; Hardy, H. and Allsop, D. (1991) *Trends in Pharmacological Science* 12:383), and abnormal calcium homeostasis and/or calcium activated kinases. (Mattson, M. P., et al. (1992) *Journal of Neuroscience* 12:376; Borden, L. A., et al. (1991) *Neurobiology of Aging* 13:33; Peterson, E., et al. (1989) *Annals of New York Academy of Science* 568:262; Peterson, C., et al. (1988) *Neurobiology of Aging* 9:261; Peterson, C., et al. (1986) *Proceedings of the National Academy of Science* 83:7999).

Alzheimer's disease is well characterized with regard to neuropathological changes. However, abnormalities have been reported in peripheral tissue supporting the possibility that Alzheimer's disease is a systemic disorder with pathology of the central nervous system being the most prominent. (Rizopoulos, E., et al. (1989) *Neurobiology of Aging* 10:717; Peterson (1986)).

Potassium channels have been found to change during memory storage. (Etcheberrigaray, R., et al. (1992) *Proceeding of the National Academy of Science* 89:7184; Sánchez-András, J. V. and Alkon, D. L. (1991) *Journal of Neurobiology* 65:796; Collin, C., et al. (1988) *Biophysics Journal* 55:955; Alkon, D. L., et al. (1985) *Behavioral and Neural Biology* 44:278; Alkon, D. L. (1984) *Science* 226:1037). This observation, coupled with the almost universal symptom of memory loss in Alzheimer's patients, led to the investigation of potassium channel function as a possible site of Alzheimer's disease pathology and to the current invention.

The so-called patch clamp technique and improvements thereof, have been developed to study electrical currents in cells. The method is used to study ion transfer through channels. To measure these currents, the membrane of the cell is closely attached to the opening of the patch micropipette so that a very tight seal is achieved. This seal prevents current from leaking outside of the patch micropipette. The resulting high electrical resistance across the seal can be exploited to perform high resolution current measurements and apply voltages across the membrane. Different configurations of the patch clamp technique can be used. (Sakmann, B. and Neker, E. (1984) *Annual Review of Physiology* 46:455).

Currently, there is no laboratory diagnostic test for Alzheimer's disease. Therefore, there is a great need for a method to rapidly and clearly distinguish between Alzheimer's patients, normal aged people, and people suffering from other neurodegenerative diseases, such as Parkinson's, Huntington's chorea, Wernicke-Korsakoff or schizophrenia. Although some investigators have suggested that calcium imaging measurements in fibroblasts were of potential clinical use in diagnosing Alzheimer's disease (Peterson et al. 1986, 1988, supra), other researchers using similar cell lines and techniques, have shown no difference in calcium levels in Alzheimer's and normal control fibroblasts. (Borden et al. 1991, supra). Thus, the latter work refutes the findings of the former work.

The methods for diagnosing Alzheimer's disease of the present invention using cells isolated from patients are needed and will greatly improve the now very complicated clinical diagnostic process for Alzheimer's disease. These methods are especially important because they are able to distinguish patients with Alzheimer's disease from patients with other neurodegenerative diseases.

SUMMARY OF THE INVENTION

The invention provides a method for assaying for Alzheimer's disease using cells isolated from patients. In one embodiment of the invention, the presence or absence of a particular potassium channel is measured. In a cell from a healthy control, potassium channels with slope conductances of 113 pS (picosiemens) and 166 pS are present and functional. In Alzheimer's cells, the 113 pS potassium channel is missing or nonfunctional.

In a second embodiment of the present invention, the effect of potassium channel blockers specific for the 113 pS potassium channel on intracellular calcium levels is assessed. In this method, intracellular calcium levels are found to be elevated in response to potassium channel blockers in normal cells, but not in cells from donors with Alzheimer's disease. The preferred potassium channel blocker is tetraethylammonium ("TEA") at a final extracellular concentration of 100 mM. However, other potassium channel blockers which specifically block the 113 pS potassium channel may also be used. Furthermore, when TEA is used, other final concentrations of TEA may be used as long as the level of TEA causes intracellular calcium levels to be elevated in normal cells, but not in cells from donors with Alzheimer's disease.

In a third embodiment of the invention, sample cells from a patient are contacted with an activator of intracellular calcium release, in an amount sufficient to release calcium from intracellular storage sites, and the resulting increase in intracellular calcium levels is measured. In this embodiment, both normal cells and cells from Alzheimer's patients exhibit an increase in intracellular calcium; however, the increase in Alzheimer's patients is much greater. When an inositol-1,4,5,-trisphosphate ($IP_3$) activator is used to increase intracellular calcium levels, the preferred embodiment utilizes bombesin added to a final extracellular concentration of 1 μm. However, other final concentrations can be used.

As shown in the examples, the combination of the second and third embodiments of the invention can be used in series to provide a very accurate method of diagnosing AD, with no false positives or false negatives. Furthermore, these methods are able to distinguish patients with Alzheimer's disease from patients with other neurodegenerative diseases. Cells from patients with Parkinson's disease, schizophrenia, Huntington's chorea, and Wernicke-Korsakoff exhibit responses of normal cells when treated with either TEA or bombesin.

It is not known at the present time if the defects detected by the methods of this invention appear prior to or concurrently with the clinical onset of Alzheimer's disease. However, if the former is true, it is anticipated that the methods of this invention will have predictive as well as diagnostic utility in the detection of Alzheimer's disease.

BRIEF DESCRIPTION OF THE FIGURES

FIGS. 1A to 1B. 113pS channel. (FIG. 1A). Cell attached recordings from Alzheimer and control fibroblasts. A potassium channel of ~4.5 pA unitary current size (0 mV pipette potential), with identical kinetics appeared in age-matched control (AC) and young controls (YC) fibroblasts, but was entirely absent in the recording of AD fibroblasts (FIG. 1A, bottom) Downward deflections represent the open state. (FIG. 1B). I/V relationships and slope conductances. I/V relationships and slope conductances (determined by linear regression) were almost identical within the voltage range explored, 113.2±0.9 pS (mean±S.D., n=8) for YC and 112.9±3.2 pS (n=7) for AC fibroblasts.

FIGS. 2A to 2B. 166pS channel. (FIG. 2A). Cell attached recordings from Alzheimer and control fibroblasts. A second channel (166 pS) was recorded under the same conditions from fibroblasts of all three groups (AD, YC and AC). (FIG. 2B). I/V relations and slope conductances. I/V relations as well as slope conductances [YC=174±5.7 pS, n=4; AC=169.2±2.8 pS, n=4; AD=157.6±4.7 pS, n=6 (Mean±S.D.)] were approximately the same across groups. Membrane potential was similar in control (−42.6±5.4, Mean±S.D., n=7) and in AD (−45.4±6.9, n=3) fibroblasts.

FIG. 3A to 3C. FIG. 3A and 3B. Percent of cells responding to the addition of 50 mM potassium chloride and average $[Ca^{2+}]_i$ (nM) of responding cells. High potassium-induced depolarization caused $[Ca^{2+}]_i$ elevation (at least 100% increase) in all three groups (AD N=13 cell lines; AC N=10, YC N=6). The proportion of responding cells and the $[Ca^{2+}]_i$ peak values were significantly higher in YC (n=183 cells) fibroblasts ($\chi^2$=14.22, p<0.001), as compared to AC (n=299) and AD (n=268) fibroblasts (FIGS. 3A and 3B). (FIG. 3C). Sample traces of time courses of the $Ca^{2+}$ response in cells after the addition of 50 mM KCl. The $[Ca^{2+}]_i$ peak occurs 10 to 15 seconds after stimulation, returning to basal levels after 100 seconds. No responses were observed if external $[Ca^{2+}]$ was lowered ["nominally $Ca^{2+}$ free" solution, 5 mM EGTA was added (estimated free $Ca^{2+}$=0.04 μM)], or $Ca^{2+}$ channel blockers (0.1 mM $LaCl_3$, 10 mM $CoCl_2$, 10 mM $NiCl_2$, 10 mM $CdCl_2$ or 10 μM nifedipine) were added before stimulation ("0 $Ca^{2+}$").

FIGS. 4A to 4C. $[Ca^{2+}]_i$ elevation in response to TEA. (FIG. 4A) Percentage of cells responding to the addition of TEA and (FIG. 4B) Average $[Ca^{2+}]_i$ response in the cells after TEA treatment. 1 mM TEA application elevated $[Ca^{2+}]_i$ in YC fibroblasts (n=130 cells) but not in AC (n=184) or AD fibroblasts (n=195). 10 mM TEA elevated $[Ca^{2+}]_i$ in YC (n=176 cells), AC (n=231), but not in AD (n=204) fibroblasts ($\chi$ 134.00, p<0.001) . Similarly, 100 mM TEA elevated $[Ca^{2+}]_i$ in YC (n=532 cells), AC (n=417), but not in AD (n=738) fibroblasts, $\chi^2$ 231.44, p<0.001 (also see Table 2). Basal $[Ca^{2+}]_i$ levels were virtually the same (S.E.<2 nM), therefore, standard error bars are not distinguishable from the bar representing the arithmetic mean for those groups. (FIG. 4C). Time course of $Ca^{2+}$ responses. The $[Ca^{2+}]_i$ peak occurs 20 to 30 seconds after 100 mM TEA addition in YC and AC fibroblasts, returning to basal levels after 100 seconds. Note that no response meeting criterion (10% of cells in a line with ≧100% elevation) was observed in AD cells. Similarly, the response was absent in control cells when external $[Ca^{2+}]$ was lowered.

FIGS. 5A to 5B. (FIG. 5A) $Ca^{2+}$ mobilization induced by 1 μm bombesin in the absence of extracellular calcium. (FIG. 5B). $Ca^{2+}$ responses at 42 sec after 1 μM bombesin application. The $[Ca^{2+}]_i$ levels in AD cells are much larger than in AC and YC cells. The numbers of cell lines (N) are 9, 8 and 6 for AD, AC and YC, respectively. The values are means ±S.E.M.

FIGS. 6A–6B (FIG. 6A). $Ca^{2+}$ responses induced by 1 μm bombesin in the presence of extracellular calcium. 1 μm bombesin elicited a fast peak of $[Ca^{2+}]_i$, followed by a sustained phase for YC and AC cells, but not for AD cells, in the presence of extracellular 2.5 mM $CaCl_2$. The arrow indicates drug application. (FIG. 6B). Bar graph illustrating differences evident 90 seconds after bombesin application. In the presence of normal extracellular calcium (2.5 mM), a sustained calcium entry follows the initial bombesin response in control cells but is completely absent in AD fibroblasts. The difference evident 90 seconds after bombesin application is shown and has a significance level of p<0.001.

DETAILED DESCRIPTION OF THE INVENTION

Figure 1B:
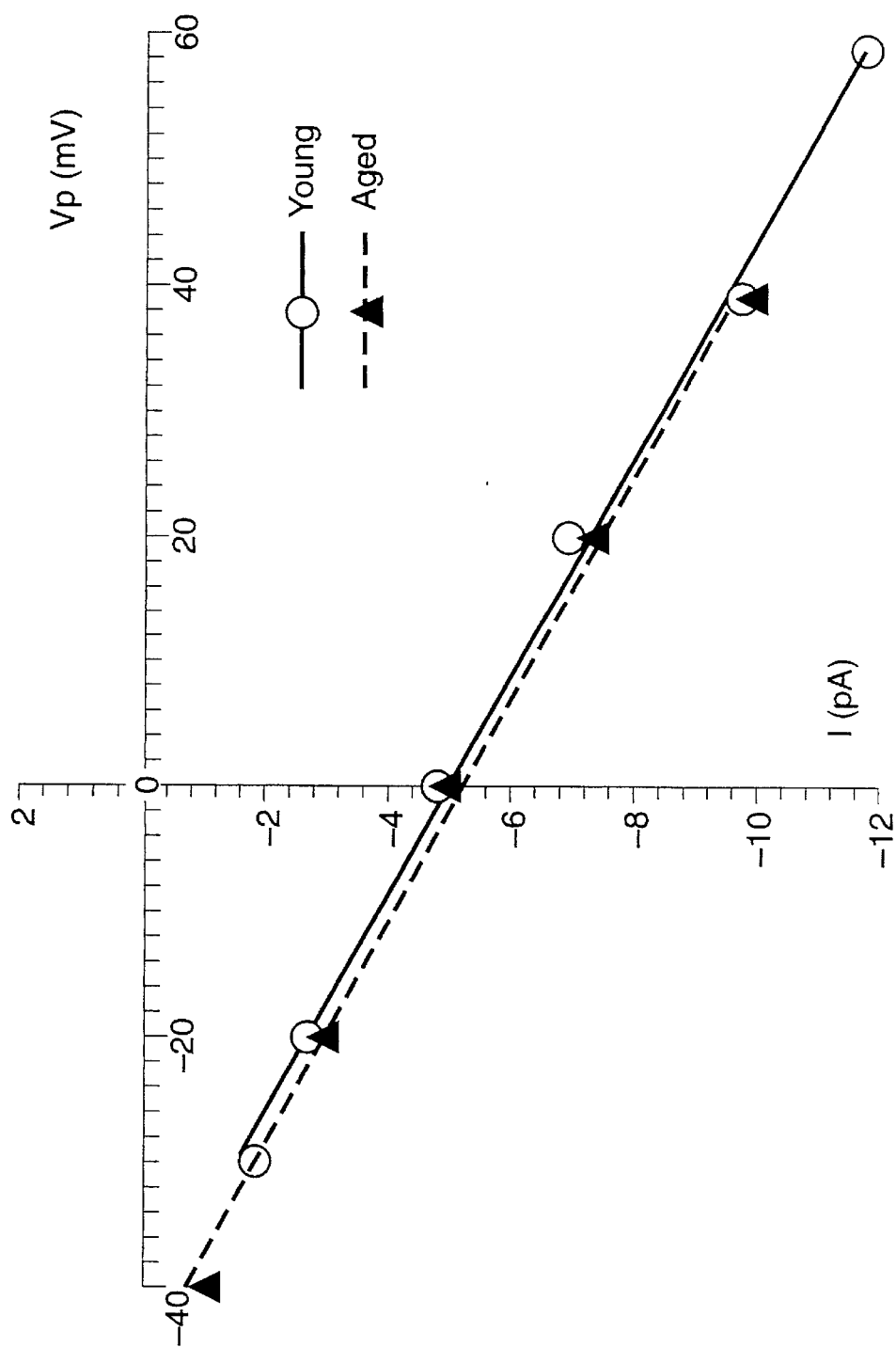

The invention concerns methods of diagnosing Alzheimer's disease (AD). These methods are based upon detecting the absence of a particular potassium ion channel in the cells of an AD patient; upon differences in intracellular calcium ion concentration in AD and non-AD cells in response to potassium channel blockers specific for the potassium ion channel that is absent in the cells of an AD patient; and differences between AD and non-AD cells in response to activators of intracellular calcium release such as activators of inositol-1,4,5-trisphosphate ($IP_3$).

The first embodiment of the invention is based upon the discovery by the inventors that cells from people not suffering from AD have (at least) two types of functional potassium channels, with conductances of 113 pS (picosiemens) and 166 pS, as measured by the patch clamp technique (see Example 1). The 113 pS channel is either missing or not functioning in people with AD. The first embodiment of the invention involves diagnosing AD by determining whether cells of the patient have a functioning 113 pS potassium channel. The presence of a functioning 113 pS potassium channel indicates that the patient does not have AD. However, the absence of a functioning 113 pS potassium channel indicates that the patient does have AD.

In this embodiment of the invention, a suitable method of recording electrical conductances in the cells must be used to detect functional potassium channels in cells. Any technique which can measure electrical conductances in a cell can be used. Examples include intracellular microelectrode recording (indirect measurement), two microelectrode voltage clamp, and single microelectrode voltage clamp. The patch clamp technique, as described herein, is a preferred method for measuring electrical conductance in small structures. In an embodiment of the invention, the cell attached mode of the patch clamp technique is used to record the existence of potassium channels and the inside-out and outside-out patch configurations are used to record the sensitivity of potassium channels to various chemicals.

The second embodiment of the invention concerns another method for diagnosing AD. In this second embodiment, the cells are contacted with a potassium channel blocker that blocks the 113 pS channel but not the 166 pS channel. This blocker may substantially block the 113 pS channel but not substantially block the 166 pS channel. An example of such a blocker is TEA, or tetraethylammonium. The blocker has the effect in non-AD cells of transiently increasing intracellular $Ca^{2+}$ concentrations. In AD cells, the blocker has substantially no effect, allowing for variation within observational or technical error. In contrast, the intracellular calcium ion concentration increases several fold in non-AD cells after being exposed to 100 mM TEA (see FIG. 4B). The intracellular $Ca^{2+}$ concentration can be measured in various ways, such as by adding fluorescent indicators or absorbance indicators or by using a $Ca^{2+}$ electrode. Preferably, because of ease of operation, fluorescent indicators are used.

Figure 4B:
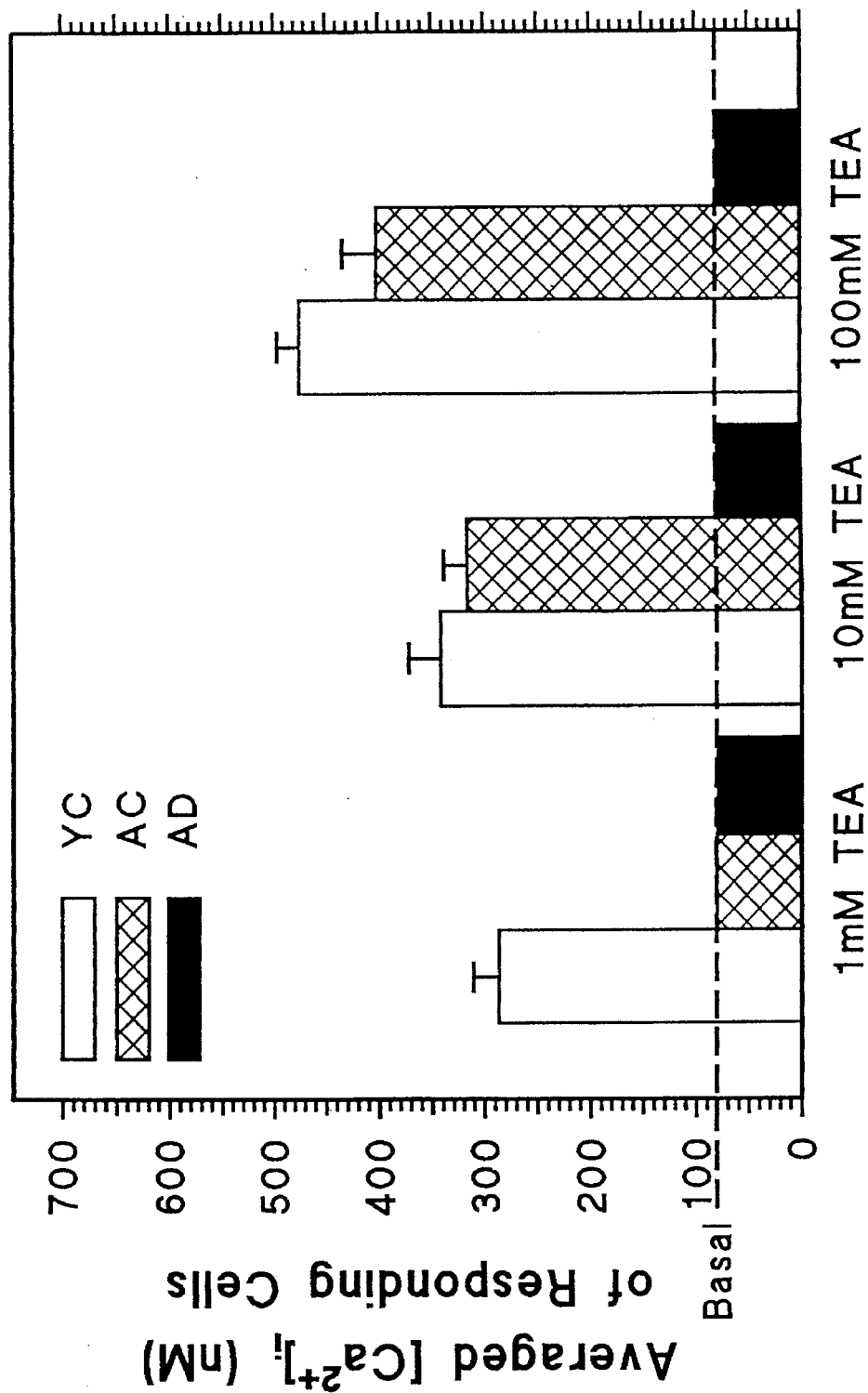
Figure 4C:
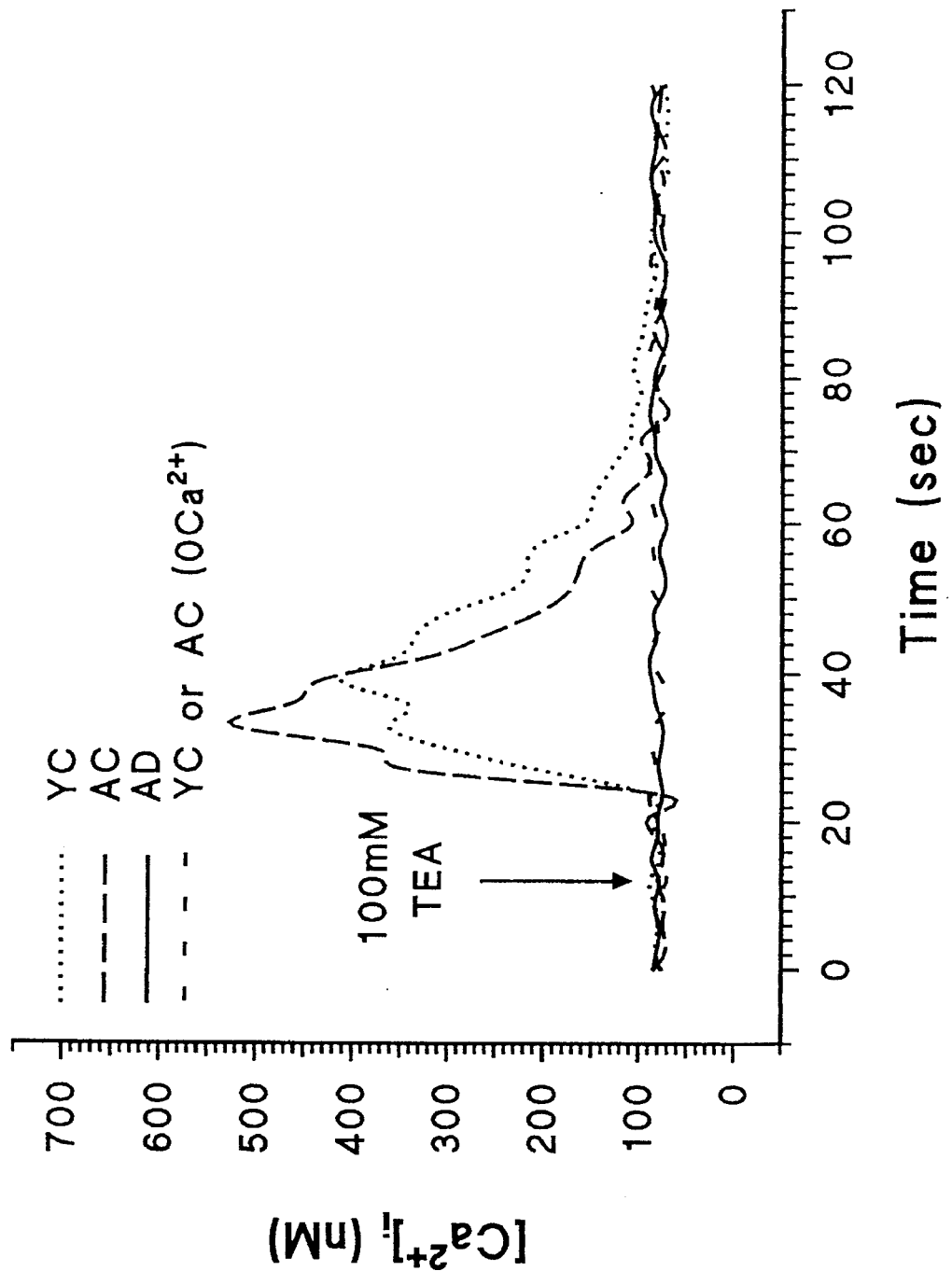

In this embodiment of the invention, the cells are first cultured with a $Ca^{2+}$ indicator, such as quin or fura-2, that fluoresces with an intensity proportional to the calcium concentration. The cells are then contacted with a select potassium channel blocker that has the ability to block the 113 pS channel but not the 166 pS channel. The fluorescence intensity of the cells before and after the addition of the potassium channel blocker is measured. In cells from people not suffering from AD the fluorescence intensity increases rapidly, peaks and then drops back down (FIG. 4C). This shows that the blocker has the effect of increasing, transiently, the calcium ion concentration. In cells from AD patients, the fluorescence intensity is substantially the same before and after the blocker is added. This is a reflection of the fact that the 113 pS channel is missing or nonfunctional in AD patients and thus potassium ion channel blockers that block the 113 pS channel, but not the 166 pS channel, do not have any effect on AD cells.

As mentioned above, the select potassium channel blocker used in this second embodiment of the invention is one that has the ability to block the 113 pS potassium channel but that has little or no effect on the 166 potassium channel. One example of such a blocker is TEA, with any biologically compatible counter anion. Preferably, the counterion is chloride. Other suitable potassium channel blockers can be easily found using the following method. Using the patch clamp technique described in Example 1, the 113 pS and 166 pS channels are detected in a viable human cell. The candidate potassium channel blocker is added to the culture containing the cells, and the patch clamp technique is used again. If the 166 pS channel is still functional, but the 113 pS channel is not, then the candidate blocker is suitable for use in this invention. Candidate potassium channel blockers include the known potassium channel blockers charybdotoxin, apamin, dendrotoxin, kalidotoxin, MCD-peptide, scylatoxin, barium, cesium, leiurotoxin I and noxiustoxin. As shown in Example 2, TEA concentrations between 10 mM and 100 mM worked well. It is easy to extend this range of workable concentrations by using AD and non-AD control cells.

Example 2 exemplifies the second embodiment of the invention for diagnosing AD using a select potassium channel blocker, TEA, and measuring the effect on intracellular calcium ion. This method is so simple, with a yes or no answer, that the exemplified sophisticated apparatus is not required to make the diagnosis. Any method which will tell one if the intracellular calcium ion concentrations has increased or not as a result of contact with the select potassium ion channel blocker will suffice to give a diagnosis. In the preferred method, fluorescent calcium ion indicators are used. In this case, any method which will tell one if the fluorescence of the indicator has increased or not as a result of contact of the cells with the select potassum channel blockers will suffice. Any method used must be able to make the measurements in the short time available. The calcium ion influx peaks a short time after contact with the blocker, and then decreases to the baseline value. In Example 2, the time it takes to peak is less than one minute.

A simpler method for detecting a fluorescent calcium ion indicator would involve using a fluorimeter, a device with a light source for exciting the calcium ion indicator and a light meter for measuring the intensity of a the fluorescence. Fluorimeters are well known and commercially available. At the simplest level, the calcium ion indicator is added to the cells taken from the patient (either fresh or expanded in culture). After an hour or so of being in contact with the indicator (at about 2 micromolar concentration) the cells in suspension are placed in the fluorimeter and the fluorescence intensity from the indicator is measured. Then the select potassium channel blocker is added; if TEA is used, it is added to a concentration of about 100 mM. The fluorescence is measured again. If the intensity, within a time period between 20 seconds and 40 seconds, is substantially the same as before the TEA was added (taking account of changes in volume due to the addition of the TEA), then a positive diagnosis of AD is made. If the intensity increases within 30 seconds and subsides after another 30 seconds, then the patient does not have AD.

It is within the skill of the art to improve the simple scheme outlined above. For example, one could use a fluorimeter with dual sample holders, in which the difference in fluorescence from two samples is measured. Starting with identical samples of patient's cells (after incubation with the indicator) in each sample holder, the select potassium channel blocker is added to only one of the samples. If there is no change in the difference signal (that is, it remains as essentially zero), a diagnosis of AD is made. If the difference signal changes significantly, then the patient does not have AD. The advantage of the differences method is that it has a built in control which increases the accuracy of the measurement. It is still within the skill of the art to add the select potassium channel blocker automatically and to make more than one measurement at a time; i.e., to automate the method for a commercial medical laboratory. Before making any diagnoses using the methods taught here, the methods should be optimized for the particular apparatus and conditions in the laboratory by using non-AD and AD control cells, which are commercially available.

The third embodiment of the invention is yet another method of diagnosing AD. This method concerns the effect of agents that activate inositol-1,4,5,-trisphosphate ($IP_3$) or otherwise induce the release of calcium from intracellular storage sites. Such storage sites include the endoplasmic reticulum and other organelles that have receptors for $IP_3$. The preferred $IP_3$ activator is bombesin. Other agents that activate the release of calcium from intracellular stores which are useful in the invention include thrombin, bradykinin, prostaglandin $F_{2\alpha}$ and vasopressin. See, e.g., Berridge, M. J. and Irvine, R. F. (1984) Nature 312:135).

It has been discovered that cells from people not suffering from AD and cells from people suffering from AD both transiently release calcium ion in response to bombesin, but the resulting intracellular calcium concentration is much larger in AD cells than in non-AD cells. The determination is easily made using any method of measuring intracellular calcium ion concentration, as discussed above with respect to the second embodiment of the invention. Again, the use of flourescent calcium indicators is the preferred method. The same experimental setup as described above for measuring fluorescence intensity can be used, i.e., a fluorimeter. In this method, it is also possible to standardize the fluorescence apparatus using non-AD and AD cells as controls. In this way, later measurements of just the patient's cells can provide a diagnosis. Alternatively, the patient's cells can be compared with non-AD cells as a control.

Figure 5A:
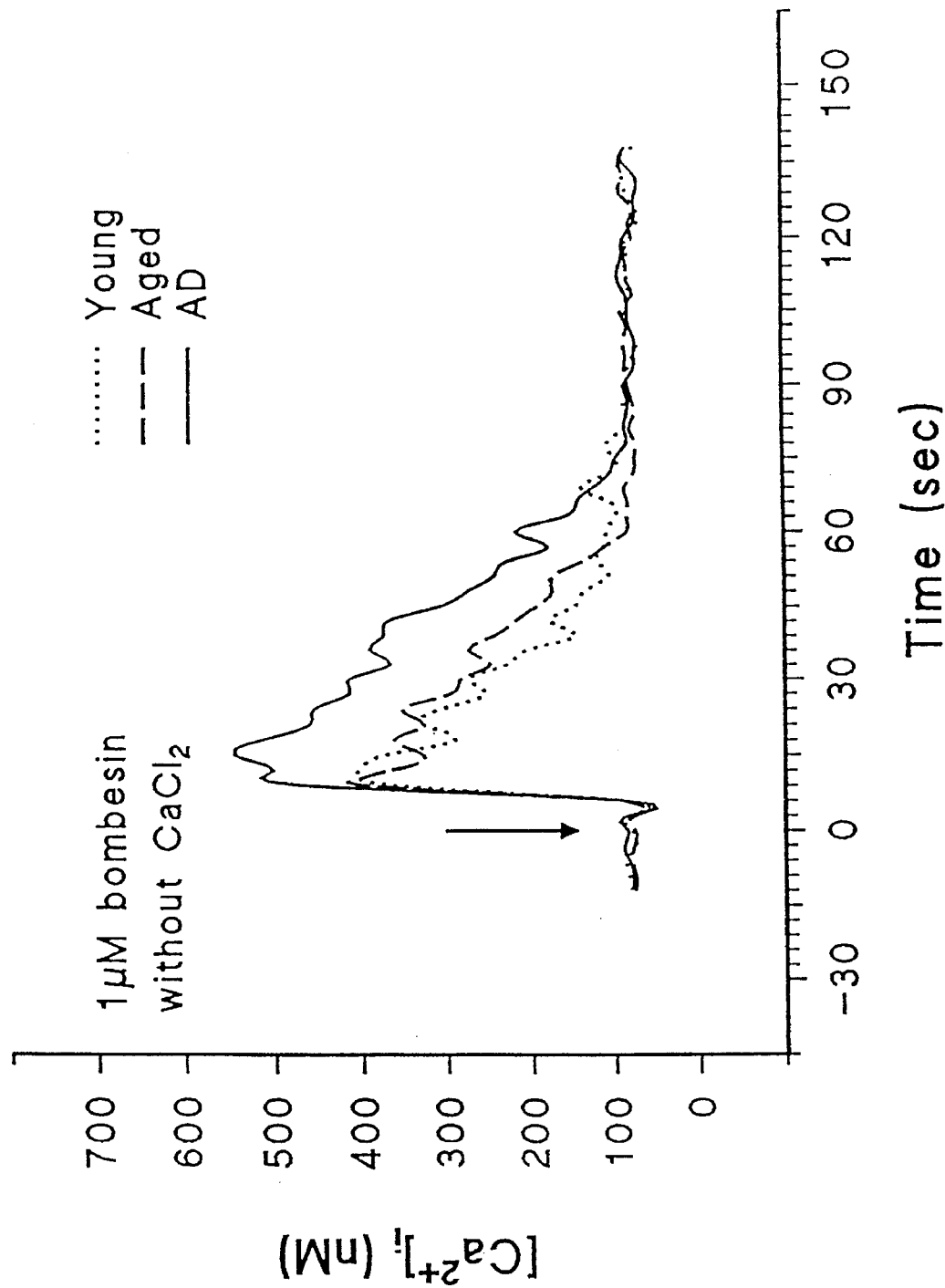

Example 3 exemplifies the third embodiment of the invention concerning the diagnosis of AD using activators of $IP_3$ and measuring their effect on calcium ion release into the cytosol from intracellular storage sites after contact with said activators. The amount of released calcium is larger in AD cells compared to non-AD cells. The increase in intracellular calcium concentration is transient: the concentration peaks soon after contact with the activator and is back to baseline value with 90 seconds. This effect is enhanced when the extracellular calcium ion concentration is zero or near zero (which is generally accomplished by washing the cells with BSS nominally free of calcium, however, other methods of tying up or negating the effect of the extracellular calcium ions can be used, such as adding EDTA, or adding a calcium channel blocker such as nifedipine, respectively). After contact with an $IP_3$ activator, such as bombesin, the intracellular calcium ion concentration in AD cells reaches a higher peak value and takes longer to return to the baseline value than either young or aged control cells (FIG. 5A). In the experimental setup described in Example 3, it was found that 42 seconds after the bombesin was added to the cells that the difference between the intracellular calcium ion concentrations in AD cells and in control cells was at a maximum, and that at that time period, i.e., at 42 seconds after bombesin was applied, the concentration of calcium ions was always greater than 300 nM in AD cells and was always less than 300 nM in control non-AD cells (FIG. 5B). Basal levels of both AD and non-AD fibroblasts were at 80 nM±0.5 nM. However, it should be noted that control values might differ from 80 nM, necessitating a criterion level of calcium signal greater or less than 300 nM. Furthermore, differences in measuring conditions might require a time longer or briefer than 42 seconds to show maximal differences between the calcium signals of AD and non-AD fibroblasts.

Again, it is not necessary to use the sophisticated methods and apparatus exemplified herein. This method of diagnosing AD can be performed more simply. One need not measure the absolute concentration of intracellular calcium; a measurement of its relative value will also work. In Example 3, the basal level of intracellular calcium ion concentrations in resting (i.e., nonactivated) cells was the same for both AD and control non-AD cells, 80 nM±0.5 nM. Thus, at the time where the concentration differences between AD and non-AD cells was maximum (i.e., at 42 seconds using bombesin and the inventors' apparatus, but the time would need to be worked out empirically for different activators and different setups) the intracellular calcium concentration in non-AD cells would be less than (300/80=) 3.75 times the basal level whereas the intracellular calcium concentration in AD cells would be greater than (300/80=) 3.75 times the basal level. Using commercially available AD and non-AD cells, one can easily determine the time at which the calcium concentrations are maximally different between AD and non-AD cells. This involves measuring relative intracellular calcium concentrations for resting cells, adding bombesin or another $IP_3$ activator, following the relative calcium ion concentrations for a minute or so, and finding the time (after the activator is added) at which the difference in relative calcium ion concentrations is at its maximum. Then, for any real sample from a patient, one simply needs to measure the relative basal intracellular calcium concentration by any means known in the art, add the activator to its prescribed concentration (about 1 micromolar for bombesin), wait the predetermined time and again measure the relative intracellular calcium concentration. If the ratio of the intracellular calcium concentration "after" the addition of the activator to the intracellular calcium concentration "before" the addition of the activator is greater than 3.75, the patient has AD; if it is less than 3.75, the patient does not have AD. It is not necessary to determine the time of maximal difference in calcium concentrations—any time where there is a reproducible difference between these ratios can be used. It is only necessary to work out the particular ratios for the time chosen from known AD and non-AD control cells.

The calcium ion indicators used in the second and third embodiments include any compounds which can enter the cell, are biocompatible, and which can bind to calcium ions to produce a species whose concentration is easily measured using any physico-chemical means and is proportional to the calcium ion concentration. Preferably the means is fluorescence or absorbance. Preferable fluorescent indicators are the commercially available indicators fura-2 AM, fura-2 pentapotassium salt, quin-2, and indo-1 from Molecular Probes (Eugene, Oreg.). The Chemical Abstracts name for fura-2, AM is 5-oxazolecarboxylic acid, 2-(6-(bis(2-((acetyloxy)methoxy)-2-oxoethyl)amino)-5-(2-(2-(bis(2-((acetyloxy)methoxy)-2-oxoethyl)amino)-5-methylphenoxy) ethoxy)-2-benzofuranyl) (acetyloxyl)methyl ester. The Chemical Abstracts name for fura-2, pentapotassium salt is 5-oxazolecarboxylic acid, 2-(6-(bis(carboxymethyl)amino)-5-(2-(2-(bis(carboxymethyl)amino)-5-methylphenoxy) ethoxy)-2 -benzofuranyl). Other fluorescent calcium indicators include Fluo-3, Rhod-2, Calcium Green™, Calcium Orange™, Calcium Crimson™ Fura Red™ and Calcium Green Dextran™ (Molecular Probes (Eugene, OR)). Generally, the cells are incubated with the indicators at a concentration of about 2 micromolar for about 60 minutes. An absorbance indicator which may be used is arsenazo. Finally, calcium levels could also be measured for this invention with calcium electrodes inserted into the cells.

In the exemplified embodiment of the invention, fluorescence was measured using an imaging system under the control of a personal computer. For excitation, 340 nm and 380 nm band path filters with a neutral-density filter were used. Images of fluorescence were obtained using a dichroic mirror, barrier filter and objective lens. The whole image can be recorded or portions thereof. A Hamamatsu Photonics Argus 50 Calcium Imaging system imaging 60 cells in a microscopic field at 10× magnification was used. Fluorescence from the cells was quantified in ¼ of the field at 10× magnification. Such an imaging system (and other similar currently available systems) with its microscope could be custom designed for everyday clinical laboratory analysis of cells' calcium signals. Other instrumentation and/or measurements would have to be adapted for the use of other calcium indicators.

In the methods of the invention, the cells that are taken from the patient can be any viable cells. Preferably they are fibroblasts; buccal mucosal cells; blood cells such as erythrocytes, lymphocytes, and lymphoblastoid cells; or nerve cells such as olfactory neurons. The cells may be fresh or may be cultured (as described in the examples). The fibroblast potassium channel dysfunction and resulting absence of TEA-induced calcium signals described herein suggest that AD, which primarily affects brain cells, is likely to alter potassium channel function in many different types of cells in the body. Similarly, AD is likely to alter calcium released by bombesin and related agents in many different types of cells in the body. The methods described herein to measure potassium channel function and calcium release, therefore, should be applicable for AD diagnosis using other cell types.

A punch skin biopsy could be used to obtain skin fibroblasts from a patient. These fibroblasts might be analyzed directly with the techniques described herein or be introduced into cell culture conditions. The resulting cultured fibroblasts would then be analyzed as described for the cultured fibroblasts obtained from the Coriell Cell Repositories described below. Other steps would be required to prepare other types of cells which might be used for analysis such as buccal mucosal cells, nerve cells such as olfactory cells, blood cells such as erythrocytes and lymphocytes, etc. For example, blood cells can be easily obtained by drawing blood from peripheral veins. Cells can then be separated by standard procedures (e.g., by using a cell sorter, centrifugation, etc.) and later analyzed in suspension or on a solid support (e.g., in petri dishes).

The present invention will now be described by way of examples, which are meant to illustrate, but not limit, the scope of the invention.

Example 1

Patch-clamp Diagnostic Test

Cultured skin fibroblasts (described in Table 3) from the Coriell Cell Repositories (Camden, N.J.) were grown under highly standardized conditions. Cristafallo, V. J. and Chapentier, R. J. (1980) *Tissue Culture Methods* 6:117. The following cell lines were used for the experiments: Young Control Fibroblasts ("YC") 3652, 3651, 2987, 4390, 3377, 8399 (21.5±2.8 years, Mean ±S.D); Age-matched Control Fibroblasts ("AC") 3524, 6010, 6842, 7603, 9878 (65.2±6.0 years); and Alzheimer's Disease Fibroblasts ("AD") 6848, 7637, 5809, 8170, 6840, 8243, 6263 (60.6±6.8 years). Five AD lines were from familial patients. Some of the lines (2 AC and 4 AD) were from Canadian kindred.

In agreement with the literature, the data indicate the time to phase out does not vary between the AD and control lines (YC and AC). Cells were seeded (approximately 5 cells per $mm^2$) in 35 mm Nunc petri dishes in Dulbecco's Modified Eagle Medium (DMEM, Gibco), supplemented with 10% fetal calf serum and used when cell density was equivalent for all cell lines, between days 2 and 4 after plating. On average, fibroblasts from AD patients and controls took the same time to reach erosion density (50 cells/$mm^2$).

Patch-clamp experiments were performed at room temperature (21°–23° C.), following standard procedures set forth in Sakmann, B. and Neher, E. (1983) Single Channels Recordings (Plenum New York) and Kukuljan, M., et al. (1991) *J. Membrane Biol.* 119:187. Before recordings, culture medium was replaced with the following solution: 150 mM NaCl, 5 mM KCl, 2 mM $CaCl_2$, 1 mM $MgCl_2$, 10 mM HEPES (NaCl) pH=7.4. Pipettes were made from Blue Tip capillary tubes (I.D. 1.1–1.2 mm) using a BB-CH Mecanex puller, and then filled with a high potassium solution of 140 mM KCl, 2 mM $CaCl_2$, 1 mM $MgCl_2$, 10 mM HEPES (NaOH), pH=7.4. Pipette resistances were approximately 6 MΩ. Records were obtained using an Axopatch-1C amplifier (dc-10 kHz), stored on tape (Toshiba PCM-video recorder), and later transferred to a personal computer using an Axolab interface. Only recordings lasting for at least 3 minutes were considered for final analysis. The pClamp suite of programs was used for single-channel data acquisition and analysis. Amplifier, interface and software were obtained from Axon Instruments (Foster City, Calif.).

In the cell-attached mode, two types of potassium channels were recorded from human skin fibroblasts. Since pipettes were filled with a high potassium solution, potassium currents were inward as expected, and their reversal potential approximately corresponded to the cell resting potential. A potassium channel (113 pS) of approximately 4.5 pA unitary current size (0 mV pipette potential), with identical kinetics appeared in YC and AC fibroblasts, but was entirely absent in the recording of AD fibroblasts (FIG. 1A). Downward deflections represent the open state. I/V relationships of the same channels in FIG. 1A (FIG. 1B) and slope conductances (determined by linear regression) were almost identical within the voltage range explored, 113.2±0.9 pS (Mean±S.D., n=8)) for YC and 112.9±3.2 pS (n=7) for AC fibroblasts.

Figure 2A:
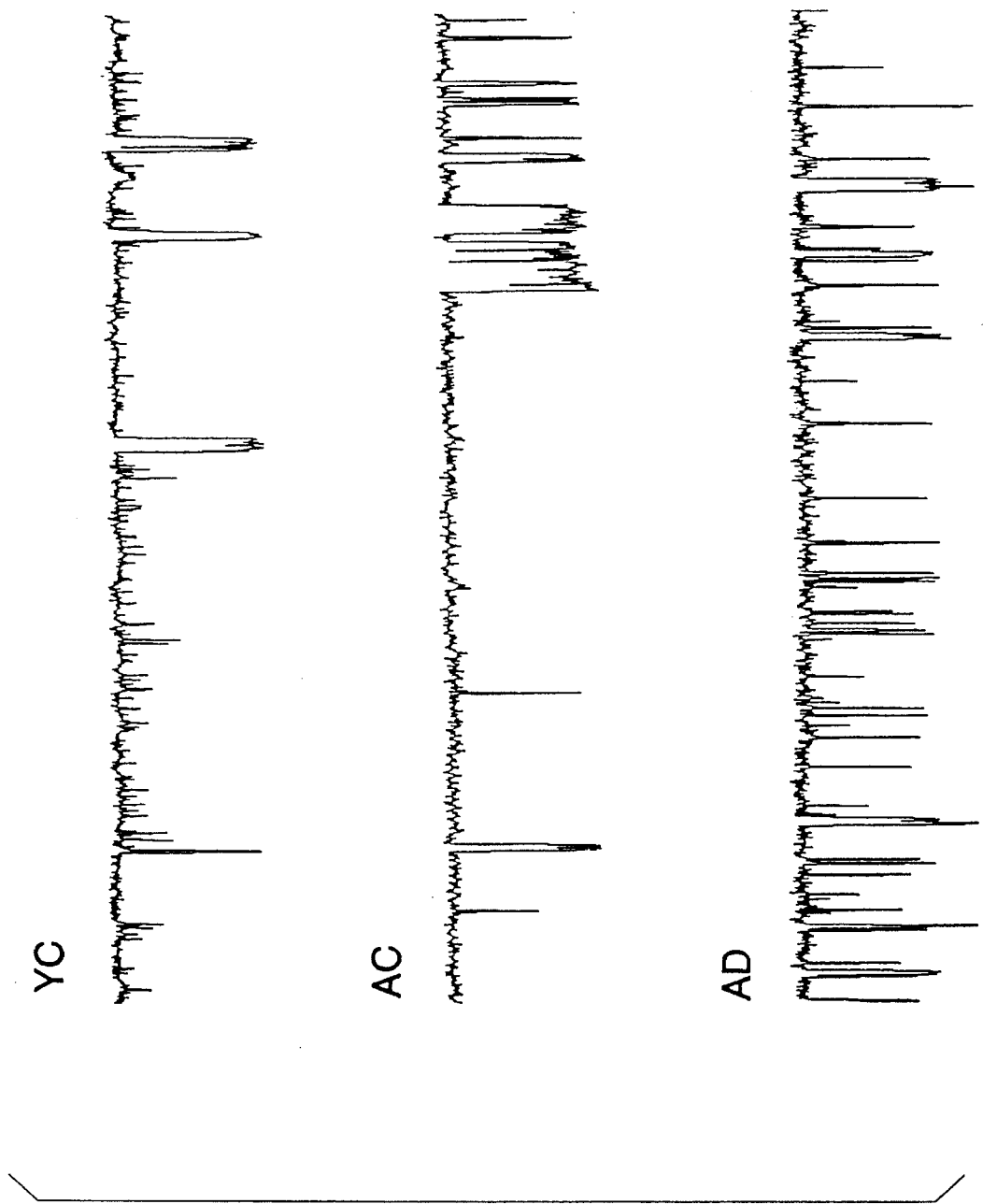

A second channel (166 pS) was recorded under the same conditions from fibroblasts of all three groups (FIG. 2A). I/V relations (FIG. 2B) as well as conductance (YC=173.4±5.7 pS, n=4; AC=169.2±2.8 pS, n=4; AD=157.6±4.7 pS, n=6 (Mean±S.D.)) were approximately the same across groups. Membrane potential was similar in control (42.6±5.4, Mean±S.D., n=7) and in AD (−45.4±6.9, n=3) fibroblasts.

Both channels had linear voltage-current relationships, with slope conductances of 113 pS and 166 pS respectively (FIGS. 1 and 2). At 0 mV pipette potential, the channels could easily be identified by their unitary current size (FIGS. 1A and 2A) and by their percentages of open time, approximately 60% for the 113 pS $K^+$ channel and approximately 10% for the 166 pS $K^+$ channel. For both channels, the percentages of open time showed no significant voltage-dependence (+60 to −40 mV pipette potential). The 113 pS $K^+$ channel was found in 47% of YC cells (n=30) and 94% of the AC cells (n=17), while it was never found in AD fibroblasts (n=24) ($\chi^2$= 18.96, p<0.001 (Table 1)). There were no AD cell lines (N=6) that had fibroblasts with an observable 113 pS channel. By contrast, all AC cell lines (N=5) and three of six YC cell lines had fibroblasts with observable 113 pS channels ($\chi^2$=11.93, p<0.005 (Table 2)). The 166 pS channel found was similar frequency in all three groups ($\chi^2$=0.89, N.S. (Tables 1 and 2)).

The 113 pS channel found to be "absent" in the AD fibroblasts, could be present but not functional.

Such dysfunction could involve structural changes in the channel and/or alteration in processes involved in channel activity regulation.

Using cell-free patches, following the method described above, it was observed that both channels were sensitive to 50 mM $Ba^{2+}$ (inside-out, n=4 for each channel), but only the 113 pS channel was sensitive (outside-out, n=4 YC, n=3 AC) to the $K^+$ channel blocker tetraethylammonium (TEA). The TEA-blockade of the 113 pS channels (possibly together with other channels) significantly affects membrane potential since control cells (n=4) depolarized 13–20 mV after 100 mM TEA addition.

TABLE 1

| Condition | Number of Cells | | |
|---|---|---|---|
| | Total | 113 pS $K^+$ Channel | 166 pS $K^+$ Channel |
| Young Controls | 30 | 14 (47%) | 6 (20%) |
| Aged Controls | 17 | 16 (94%) | 6 (35%) |
| Alzheimer Patients | 24 | 0 (0%) | 8 (33%) |

TABLE 2

| Condition | Number of Cell Lines | | |
|---|---|---|---|
| | Total | 113 pS $K^+$ Channel | 166 pS $K^+$ Channel |
| Young Controls | 6 | 3 | 4 |
| Aged Controls | 5 | 5 | 3 |
| Alzheimer Patients | 7 | 0 | 4 |

When using control cells, it is best to use age-matched control cells.

Example 2

TEA-$Ca^{2+}$ Diagnostic Test

Cultured skin fibroblasts (described in Table 3) from the Coriell Cell Repositories (Camden, N.J.) were grown as described in Example 1.

Thirteen AD, ten AC, and six YC were used for the calcium-imaging experiments. Culture medium was replaced and washed three times with basal salt solution ("BSS") consisting of 140 mM NaCl, 5 mM KCl, 2.5 mM $CaCl_2$, 1.5 mM $MgCl_2$, 5 mM glucose, 10 mM HEPES (NaOH), pH 7.4. Nominally $Ca^{2+}$ free BSS was prepared as BSS without adding $CaCl_2$.

Fura-2 (acetyloxymethyl ester) (Fura-2AM) was purchased from Molecular Probes (Eugene, OR) and stored as a 1 mM solution in dimethylsulfoxide. Fura-2AM was added to a final concentration of 2 μM and cells were incubated at room temperature (21°–23° C.) for 60 minutes. After incubation, cells were washed at least three times with BSS at room temperature before $[Ca^{2+}]_i$ determinations. Fluorescence was measured with a Hamamatsu ARGUS 50 imaging system (Hamamatsu Photonics, Japan) under the control of a personal computer (Hamamatsu imaging software package). Excitation at 340 nm and 380 nm was attenuated with neutral density filters. Fluorescent images were obtained with a 400 nm dichroic mirror and a 510 nm long-pass barrier filter. The objective lens was an X10 Nikon UV fluor. Fluorescence was measured within a uniformly illuminated fraction (¼) of the whole image.

The averaged $Ca^{2+}$ responses within 15×15 pixels in cytosolic and in nuclear cellular compartments obtained were quantified with ratios between emitted 510 nm fluorescence activated at 340 nm and fluorescence emitted at 510 nm with activation at 380 nm. These ratios were transformed to absolute values of $[Ca^{2+}]$, after calibration based on the following equation:

$$R=R_{max}+(R_{min}-R_{max})/(1+([Ca^{2+}]_i/Kd)^b)$$

Here R denotes fluorescence intensity illuminated by 340 nm divided by fluorescence intensity illuminated by 380 nm (F340/F380), and $R_{max}$ and $R_{min}$ are the values of R when the concentration of calcium is at a maximum and a minimum (i.e., the maximum and minimum value measurable by the machine under the measuring conditions), respectively. Kd is a dissociation constant of fura-2 for $Ca^{2+}$ and was determined as 240 nM. The value of b, which determined the degree of asymmetry, was 1.2. TEA application caused a minimum of 100% $[Ca^{+2}]_i$ elevation in at least 18% of cells in every control cell line except one young control. A response of 100% $[Ca^{+2}]_i$ elevation in at least 10% of cells in a line was, therefore, considered to be a conservative criterion for a positive response. Only one AD cell line had cells with any response (100% $[Ca^{+2}]_i$ elevation in 4% of cells), well below the criterion).

Figure 3B:
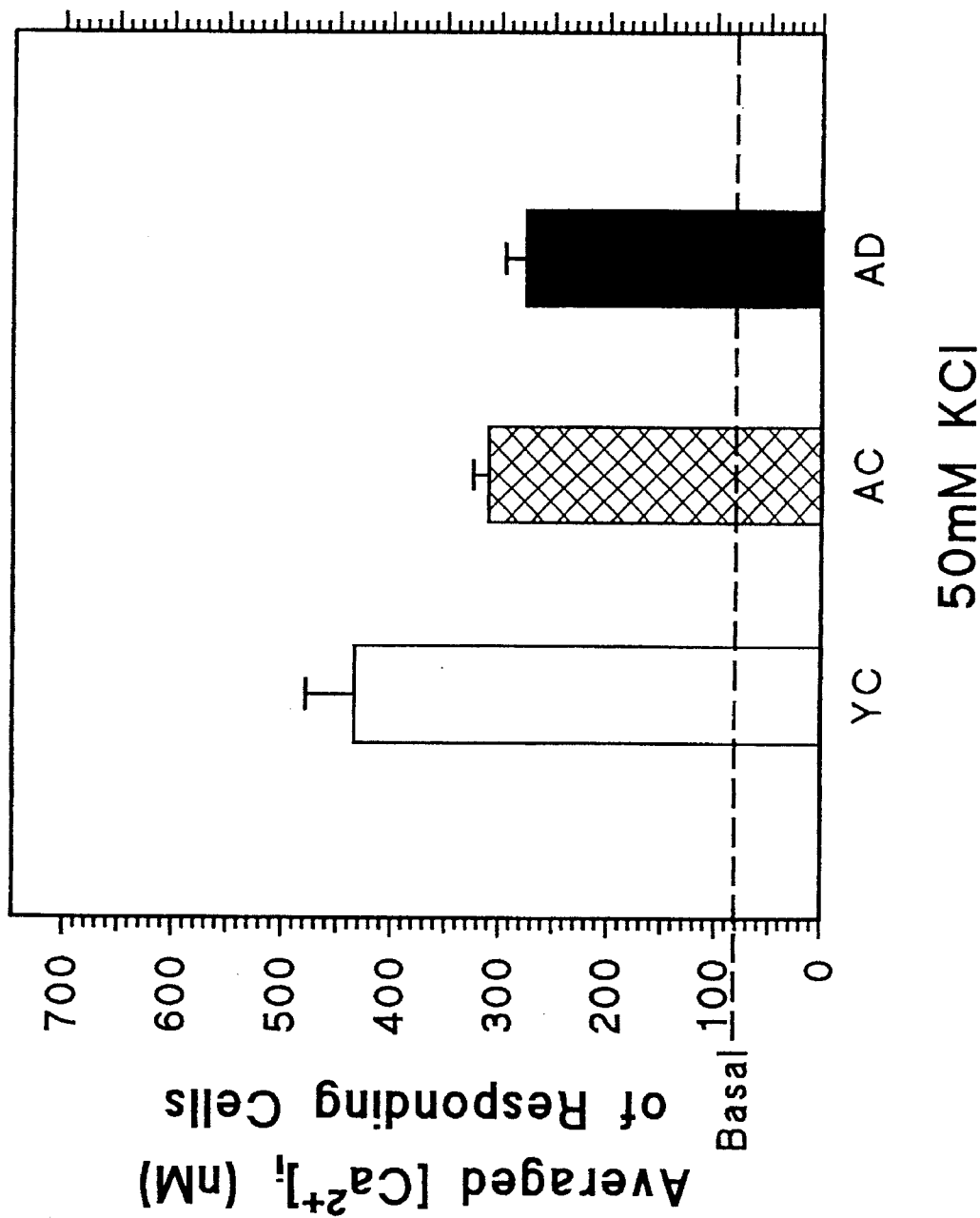

Depolarization of the fibroblasts by perfusion in elevated external potassium caused greater elevation of intracellular $Ca^{2+}$ ($[Ca^{2+}]_i$) in YC as compared to AC and AD cells (FIG. 3). This depolarization-induced $[Ca^{2+}]_i$ elevation was eliminated by lowering external calcium or by adding calcium channel blockers (FIG. 3C). High $K^+$-induced depolarization caused a marked $[Ca^{2+}_i]$ elevation (at least 100% increase) in all three groups (AD, n=13 cell lines; AC, n=10; YC, n=6). The proportion of responding cells and the $[Ca^{2+}]_i$ peak values were significantly higher in YC (n=183 cells) fibroblasts ($\chi^2$=14.22, p<0.001), as compared to AC (n=299) and AD (n=268) fibroblasts. The $[Ca^{2+}]_i$ peak occurs 10 to 15 seconds after stimulation, returning to basal levels after 100 seconds. No responses were observed if external calcium was lowered by addition of "nominally $Ca^{2+}$ free" solution or 5 mM EGTA (estimated free $Ca^{2+}$=0.04 μM) or $Ca^{2+}$ channel blockers (0.1 mM $LaCl_3$, 10 mM $CoCl_2$, 10 mM $NiCl_2$, 10 mM $CdCl_2$ or 10 μM nifedipine) before stimulation.

Depolarization of control fibroblasts by TEA also caused $[Ca^{2+}]_i$ elevation, that was eliminated by lowering external calcium or by adding calcium channel blockers. AD fibroblasts, however, only showed $[Ca^{2+}]_i$ elevation in elevated external potassium and had no $[Ca^{2+}]_i$ response with addition of even 100 mM TEA. Every AC cell line (N=10) and all but one YC cell line (N=6) had cells responding to TEA, while none of the thirteen AD cell lines examined had cells responding to 100 mM TEA ($\chi^2$=25.66, p<0.001) (Tables 3 and 5).

TABLE 3

| Condition | Number of Cell Lines | |
|---|---|---|
| | Total | Increase in $[Ca^{+2}]_i$ with 100 mM TEA |
| Young Controls | 6 | 5 |
| Aged Controls | 10 | 10 |
| Alzheimer's Patients | 13 | 0 |

1 mM TEA application elevated $[Ca^{2+}]_i$ in YC fibroblasts (n=130 cells) but not in AC (n=184) or AD (n=195) fibroblasts. 10 mM TEA elevated $[Ca^{2+}]_i$ in YC (n=176) and AC (n=231) but not in AD fibroblasts(n=204). Similarly 100 mM TEA elevated $[Ca^{2+}]_i$ in YC (n=532) and AC (n=417), but not in AD fibroblasts (n=738) ($\chi^2$=231.44, p<0.001). At least 417 cells were explored in each experimental group (Table 4). The $[Ca^{2+}]_i$ values of the responding cell were similar in YC and AC cells after 10 and 100 mM TEA addition. Basal $[Ca^{2+}]_i$ levels were virtually the same (S.E.<0.5 nM), therefore standard error bars are not distinguishable from the bar representing the arithmetic mean for those groups (FIG. 4B). Time courses of $Ca^{+2}$ response shows that the $[Ca^{2+}]_i$ peak occurs 20 to 30 seconds, after 100 mM TEA addition in YC and AC fibroblasts, returning to basal levels after 100 seconds. No response was observed in AD cells (10% of cells in a line with ≧100% elevation).

response to TEA is almost certainly due to dysfunction of $K^+$ channels and not to $Ca^{2+}$ channel dysfunction.

The $[Ca^{2+}]_i$ measurements are in agreement with the patch-clamp measurements insofar as they both indicate potassium channel dysfunction in the AD fibroblasts. See Table 5.

TABLE 5

| Line # | Age | Gender | Race | Diag. Criteria | 113 K+ Channel | TEA Response Non Blind | TEA Response Blind |
|---|---|---|---|---|---|---|---|
| *Alzheimer's Disease Fibroblasts* | | | | | | | |
| AG06840+[1] | 56 | M | W | Clinical — Fam. H. | − | − | − |
| AG06848+[2] | 55 | F | W | Clinical — Fam. H.* | − | − | N.T. |
| AG07637+ | 55 | F | W | Clinical — Fam. H. | − | − | − |
| AG08170+ | 56 | M | W | Clinical — Fam. H. | − | − | − |
| AG06844+ | 59 | M | W | Clinical — Fam. H.* | N.T. | N.T. | − |
| AG04400‡ | 61 | F | W | Clinical — Fam. H. | N.T. | N.T. | − |
| AG04401‡ | 53 | F | W | Clinical — Fam. H.* | N.T. | − | − |
| AG05809 | 63 | F | W | Clinical — Fam. H. | − | − | N.T. |
| AG08243 | 72 | M | W | Clinical — No Fam. H. | − | − | − |
| AG07375 | 71 | M | W | Clinical — No Fam. H. | N.T. | − | − |
| AG07376 | 59 | M | W | Clinical — No Fam. H. | N.T. | − | − |
| AG06263 | 67 | F | W | Clinical — No Fam. H. | − | − | − |
| AG07377 | 59 | M | W | Clinical — No Fam. H. | N.T. | N.T. | − |
| *Age-Matched Control Fibroblasts* | | | | | | | |
| GM03524 | 67 | F | B | Normal | + | + | N.T. |
| AG06010 | 62 | F | W | Normal | + | + | + |
| AG06842+ | 75 | M | W | Normal—Fam. H. | + | N.T. | N.T. |
| AG07603+ | 61 | F | W | Normal—Fam. H. | + | + | N.T. |
| AG09878 | 61 | F | B | Normal | + | + | + |
| AG08044 | 58 | F | B | Normal | N.T. | + | N.T. |
| AG6241 | 61 | M | W | Normal | N.T. | + | N.T. |
| AG4560 | 59 | M | W | Normal | N.T. | + | N.T. |
| GM04260 | 60 | M | W | Normal | N.T. | + | N.T. |
| AG07141 | 66 | F | W | Normal | N.T. | N.T. | + |
| AG11363 | 74 | F | W | Normal | N.T. | N.T. | + |
| *Young Control Fibroblasts* | | | | | | | |
| GM03652 | 24 | M | W | Normal | + | + | + |
| GM03651 | 25 | F | W | Normal | + | + | + |
| GM02987 | 19 | M | W | Normal | − | − | − |
| GM04390 | 23 | F | W | Normal | + | + | + |
| GM03377 | 19 | M | W | Normal | − | + | + |
| GM08399 | 19 | F | ? | Normal | − | + | + |

Similarly, the response was absent in control cells when external $[Ca^{2+}]$ was lowered (FIG. 4C).

TABLE 4

| | Number of Cells | |
|---|---|---|
| Condition | Total | Increase in $[Ca^{+2}]_i$ with 100 mM TEA |
| Young Controls | 532 | 145 (27%) |
| Aged Controls | 417 | 119 (29%) |
| Alzheimer's Patients | 738 | 4 (0.5%) |

TEA-induced $[Ca^{2+}]_i$ elevations were repeated using a coded subsample that included Alzheimer's and control fibroblasts. Experiments and analyses were conducted without the experimenter's knowledge of the cell lines identity. The results were in complete agreement with the non-blind sample. None of the blindly examined AD cell lines (N=11) showed $[Ca^{2+}]_i$ elevation in response to TEA and all but one of the control cell lines (4 AC and 6 YC) had TEA responses ($\chi^2$=17.33, p<0.001 (Table 5)).

Since $[Ca^{2+}]_i$ elevation in response to high potassium was virtually the same for AC and AD cells, the lack of AD cells Alzheimer's fibroblasts were from familial (N=8) and non-familial cases (N=5). Five (+) are members of the Canadian family 964, only 1 and 2 are immediate relatives (sibs). "‡" are members (sibs) of family 747. Autopsy confirmed Alzheimer's Disease in three cases (*). Two of the age-matched control (N=11) cell lines are unaffected members of the Canadian family (964). All young control lines (N=6) are from normal and without AD family history individuals. Criterion $[Ca^{2+}]_i$ responses (to 100 mM TEA), indicates as +, were observed in all AC lines used and in all but one of the YC lines. The presence of the 113 pS $K^+$ channel is indicated by the "+" sign. None of the AD lines exhibited "positive" response. A blind protocol was conducted to measure TEA responses in Alzheimer's (N=11) and control (YC=6, AC=4) fibroblasts. The results exactly reproduced those of the non-blind sample: no AD cells line exhibited TEA responses and 9 out 10 control cells showed TEA responses, $x^2$=17.33, p<0.001. The notation "N.T." indicates cell line/conditions that were not tested.

Example 3

Bombesin—Ca$^{2+}$ Diagnostic Test

Human skin fibroblasts listed in Table 3 were used. The average age for the AD cell lines used is 60.5±5.9 years; for the AC cell lines is 62.3±9.6 years; and for the YC cell lines is 21.5±2.2 years. The method of maintenance for the cells was described in Example 1, i.e., maintained 3–5 days at 37° C. in CO$_2$/air (5%/95%) to reach a density of 50 cells/mm$^2$ before calcium measurements. The number of culture passages were less than 19.

Bombesin was purchased from Calbiochem (San Diego, Calif.). Bombesin was stored as a 1 mM solution in distilled water. Fura-2 (acetyloxymethyl ester), fura-2 (pentapotassium salt) and omega-conotoxin ($\omega$-CgTX) GVIA were from Molecular Probes (Eugene, Oreg.). Fura-2 AM was stored as a 1 mM solution in dimethylsulfoxide; fura-2 pentapotassium salt was stored as a 6mM solution in potassium acetate, and $\omega$-CgTX was stored as a 100 μM solution in distilled water. All of the chemicals except for phenytoin were maintained at −20° C. and protected from light.

The cells were incubated with 2 μM fura-2 AM in BSS (described in Example 1) at room temperature (21°–23° C.) for 60 min. After being washed at least three times with BSS, the cells were used for measurement of [Ca$^{2+}$]$_i$ at room temperature. Cell fluorescence was measured as described in Example 2. Absolute calcium values were calculated as shown in Example 2.

Bombesin was added to the cells at a final concentration of 1 μM. Calcium mobilization levels were measured from −30 seconds to 150 seconds after bombesin treatment. (FIG. 5A) The particular experimental set up resulted in a maximum difference in [Ca$^{2+}$]$_i$ between AD cells and control cells at a time of 42 seconds after bombesin was added.

Forty two (42) seconds after bombesin treatment, in the absence of extracellular Ca$^{2+}$, the [Ca$^{2+}$]$_i$ levels in Alzheimer's disease cells are much larger (p<0.0001) than in age-matched and young controls. The numbers of cell lines (N) are 10, 8, and 6 for Alzheimer's disease, age-matched and young cells, respectively. The values are means±S.E.M. (FIG. 5B).

Bombesin stimulated IP$_3$-induced Ca$^{2+}$ release from intracellular storage sites in fibroblasts from all groups, but it caused a larger and more prolonged response in AD fibroblasts. This larger and prolonged response in AD cells was independent of extracellular Ca$^{2+}$. On the other hand, the IP$_3$-mediated Ca$^{2+}$ responses in AC and YC cells were followed by Ca$^{2+}$ entry. When this Ca$^{2+}$ entry was diminished by removal of extracellular Ca$^{2+}$, or blocking with inorganic Ca$^{2+}$ blockers, the bombesin-elicited Ca$^{2+}$ responses in control cells were found to return to the basal level faster than in AD cells (FIG. 5A). The results shown in FIG. 5A are for cells washed with BSS nominally free of Ca$^{2+}$.

Since Ca$^{2+}$ influx induced by bombesin was not observed in AD cells, this pathway of Ca$^{2+}$ entry following the decrease of stored calcium seems to be altered. This test independently confirmed the diagnoses made by the previously described test based on potassium channel dysfunction. In particular, the Ca$^{2+}$ responses at 42 sec after 1 μM bombesin stimulation in AD fibroblasts in the absence of extracellular Ca$^{2+}$ were always higher than 300 nM. In contrast, the [Ca$^{2+}$]$_i$ in AC and YC were less than 300 nM and 200 nM, respectively (FIG. 5B).

In a variation on the above experiment, Ca$^{2+}$ responses were induced by 1 μm bombesin in the presence of extracellular calcium. In the presence of 2.5 mM extracellular CaCl$_2$, 1 μm bombesin elicited a fast peak of [Ca$^{2+}$]$_i$, followed by a sustained phase for YC and AC cells, but not for AD cells. (FIG. 6A). This difference was evident 90 seconds after bombesin application and with a significance level of p<0.001. (FIG. 6B). This difference in response of AD and non-AD cells to bombesin in the presence of extracellular calcium can be used to provide a "yes or no" diagnosis of AD. Detection methods similar to those described above with respect to the second embodiment of the invention involving the diagnosis of AD by detecting differences between non-AD and AD cells in response to select potassium channel blockers (e.g., TEA) may be used. Furthermore, the combination of this diagnostic test with any one of the above diagnostic tests further increases the confidence level of a correct diagnosis as AD or non-AD.

Example 4

Responses In Neuropathological Non-AD Fibroblasts

Using the techniques described in Examples 2 and 3, cells from donors with other diseases were measured for intracellular calcium levels in response to either TEA or bombesin.

Fibroblasts from a Parkinson's disease donor had normal TEA (indicated as +) and bombesin responses ("N"), and did not significantly differ from responses observed in the age-matched control group. Fibroblasts from two schizophrenic patients also had normal TEA and bombesin responses. In addition, normal TEA responses were observed in five out of seven cases of Huntington's disease, and the bombesin response was normal in all Huntington's cases. Furthermore, normal TEA and bombesin responses were observed in four out of four cases of Wernicke-Korsakoff disease (Table 6). These responses are significantly different from those of AD fibroblasts to the level of p<0.0001 (Fisher's exact test). "*" indicates autopsy confirmation.

TABLE 6

| Line # | Age | Gender | Race | Condition | TEA | Bombesin |
|---|---|---|---|---|---|---|
| AG08395 | 85 | F | W | Parkinson's* | + | N |
| GM01835 | 27 | F | W | Schizophrenia | + | N |
| GM02038 | 22 | M | W | Schizophrenia | + | N |
| GM06274 | 56 | F | W | Huntington's | + | N |
| GM02165 | 55 | M | W | Huntington's | + | N |
| GM00305 | 56 | F | W | Huntington's | − | N |
| GM01085 | 44 | M | W | Huntington's | + | N |
| GM01061 | 51 | M | W | Huntington's | + | N |
| GM05030 | 56 | M | W | Huntington's | − | N |
| GM04777 | 53 | M | W | Huntington's | + | N |
| 7504 | 50 | M | W | Wernicke-Kors. | + | N |
| 7505 | 52 | F | W | Wernicke-Kors. | + | N |
| 7507 | 63 | M | W | Wernicke-Kors. | + | N |
| 7508 | 64 | M | W | Wernicke-Kors. | + | N |

Every reference cited hereinbefore is hereby incorporated by reference in its entirety.

The invention has been described in detail with particular reference to the preferred embodiments thereof, but it will be understood that the invention is capable of other and different embodiments. As is readily apparent to those skilled in the art, variations and modifications can be affected within the spirit and scope of the invention. Accordingly, the foregoing disclosure and description are for illustrative purposes only, and do not in any way limit the invention, which is defined only by the claims.

We claim:

1. A method of indicating the presence of Alzheimer's disease in a patient, said method comprising the following steps:

a. obtaining a sample of cells from said patient; and b. detecting the presence or absence of a functioning 113 pS potassium ion channel in said cells;

the absence of said potassium ion indicating the presence of Alzheimer's disease.

2. The method of claim 1, wherein said cells are selected from the group consisting of fibroblasts, buccal mucosal cells, neurons, and blood cells.

3. The method of claim 2, wherein said cells are fibroblasts.

4. The method of claim 1, wherein said detecting step b is performed by a patch clamp technique.

5. A method of indicating the presence or absence of Alzheimer's disease in a patient, said method comprising the following steps:

a. obtaining a sample of cells from said patient;

b. measuring a concentration of intracellular calcium ion in said cells;

c. contacting said cells with a potassium ion channel blocker, said blocker having the ability to block the 113 pS potassium ion channel but not the 166 pS potassium ion channel in said cells;

d. subsequently measuring the concentration of intracellular calcium ion in said cells;

e. comparing the concentration of measured intracellular calcium in step d to the concentration of measured intracellular calcium of step b, wherein an increase in intracellular calcium concentration as measured in step d as compared to step b indicates the absence of Alzheimer's disease and no increase in concentration as measured in step d as compared to step b indicates the presence of Alzheimer's disease.

6. The method of claim 5 wherein the select potassium ion channel blocker is tetraethylammonium.

7. The method of claim 5, wherein said cells are selected from the group consisting of fibroblasts, buccal mucosal cells, neurons, and blood cells.

8. The method of claim 9 wherein said cells are fibroblasts.

9. The method of claim 5 wherein said measuring steps b and d are performed using a fluorescent calcium ion Indicator and a fluorimeter.

10. The method of claim 9 wherein said calcium ion indicator is selected from the group consisting of fura-2 AM, fura-2 pentapotassium salt and quin-2.

11. The method of claim 5 wherein the potassium ion channel blocker is selected from the group consisting of charybdotoxin, apamin, dendrotoxin, kalidotoxin, MCD-peptide, scyllatoxin, barium, cesium, leiurotoxin I and noxiustoxin.

12. A method of indicating the presence of Alzheimer's disease in a patient, said method comprising the following steps:

a. obtaining a sample of cells from said patient;

b. measuring the intracellular calcium ion concentration in said cells;

c. contacting said cells with a potassium ion channel blocker, said blocker having the ability to block the 113 pS potassium ion channel but not the 166 pS potassium ion channel in said cells; and d. measuring the intracellular calcium ion concentration in said cells after step c to determine a maximum difference in intracellular calcium ion concentration measured in steps b and d between Alzheimer's disease cells and control cells;

wherein the absence of an increase of intracellular calcium ion concentration in the cells from said patient measured in steps b and d in a time period between step c and step d indicates the presence of Alzheimer's disease.

13. A method of indicating the presence of Alzheimer's disease in a patient according to claim 12 wherein step d comprises measuring the intracellular calcium ion concentration in said cells within a time period less than one minute after said contacting step c.

14. A method of indicating the presence of Alzheimer's disease in a patient, said method comprising the following steps:

a. obtaining a sample of cells from said patient;

b. measuring the basal level concentration of intracellular calcium ion in said cells;

c. contacting said cells with an activator of intracellular calcium release;

d. measuring the intracellular calcium ion concentration in said cells at a predetermined time after the contacting step c; and e. comparing a ratio of measured concentrations of step d to step b to previously determined ratios for known Alzheimer's disease cells and non-Alzheimer's disease cells at said predetermined time;

wherein if the ratio of step e is the same as or greater than the previously determined ratio for known Alzheimer's disease cells, indicates the presence of Alzheimer's disease, and if the ratio of step e is the same as or less than the previously determined ratio for known non-Alzheimer's disease cells, indicates the absence of Alzheimer's disease.

15. The methods of claim 14 wherein the predetermined time of step d is that time when the ratio of step e is at a maximum.

16. The method of claim 14 wherein an extracellular calcium ion concentration is zero or near zero.

17. The method of claim 14, wherein said cells are selected from the group consisting of fibroblasts, buccal mucosal cells, neurons, and blood cells.

18. The method of claim 17, wherein said cells are fibroblasts.

19. The method of claim 14 wherein said measuring steps b and d are performed using a fluorescent calcium ion indicator and a fluorimeter.

20. The method of claim 19 wherein said calcium ion indicator is selected from the group consisting of fura-2 AM, fura-2 pentapotassium salt, and quin-2.

21. The method of claim 14 wherein the activator of intracellular calcium release is an $IP_3$ activator.

22. The method of claim 14 wherein the activator of intracellular calcium release is bombesin.

23. The method of claim 14 wherein the activator of intracellular calcium release is selected from the group consisting of thrombin, bradykinin, prostaglandin $F_{2\alpha}$ and vasopressin.

24. A method of indicating the presence of Alzheimer's disease in a patient, said method comprising the following steps:

a. obtaining a sample of cells from said patient;

b. measuring a basal level concentration of intracellular calcium ion in said cells in the presence of extracellular calcium;

c. contacting said cells with an activator of intracellular calcium release; and d. measuring an intracellular calcium ion concentration in said cells after the contacting step c;

wherein if the intracellular calcium ion concentration measured in step d is the same as that measured in step b, indicates the presence of Alzheimer's disease.

* * * * *

UNITED STATES PATENT AND TRADEMARK OFFICE
CERTIFICATE OF CORRECTION

PATENT NO. : 5,580,748
DATED : Decmber 3, 1996
INVENTOR(S) : Alkon, Daniel L.; Etcheberrigaray, Rene; Ito, Etsuro and Gibson, Gary It is certified that errors appear in the above-identified patent and that said Letters Patent is hereby corrected as shown below:

On the cover page:

In the Assignee, after "Washington, D.C." add -- and Cornell Research Foundation, Inc., Ithaca, NY --

In claim 6, line 1 (col. 17, line 34), delete "select" therefrom.

In claim 14, line 1 (col 18, line 8), after "presence" insert --or absence--.

Signed and Sealed this

Twenty-third Day of September, 1997

Attest:

BRUCE LEHMAN

*Attesting Officer*         *Commissioner of Patents and Trademarks*